United States Patent
Yokoyama et al.

(10) Patent No.: US 8,119,686 B2
(45) Date of Patent: Feb. 21, 2012

(54) SPIROQUINONE COMPOUND AND PHARMACEUTICAL COMPOSITION

(75) Inventors: Shinji Yokoyama, Nagoya (JP); Hashime Kanazawa, Hamura (JP); Tomoji Aotsuka, Hamura (JP)

(73) Assignee: Hykes Laboratories LLC, Aichi (JP)

( * ) Notice: Subject to any disclaimer, the term of this patent is extended or adjusted under 35 U.S.C. 154(b) by 343 days.

(21) Appl. No.: 12/312,640

(22) PCT Filed: Nov. 21, 2007

(86) PCT No.: PCT/JP2007/072547
§ 371 (c)(1),
(2), (4) Date: May 20, 2009

(87) PCT Pub. No.: WO2008/062830
PCT Pub. Date: May 29, 2008

(65) Prior Publication Data
US 2010/0056613 A1 Mar. 4, 2010

(30) Foreign Application Priority Data

Nov. 24, 2006 (JP) .................. 2006-316583
Aug. 6, 2007 (JP) .................. 2007-204024

(51) Int. Cl.
*A61K 31/385* (2006.01)
*C07D 339/02* (2006.01)
(52) U.S. Cl. ......................... 514/439; 549/35
(58) Field of Classification Search .................. 514/439; 549/35
See application file for complete search history.

(56) References Cited

U.S. PATENT DOCUMENTS 3,862,332 A * 1/1975 Barnhart et al. .............. 514/712
2007/0161702 A1 7/2007 Yokoyama et al.

FOREIGN PATENT DOCUMENTS

| EP | 1 704 857 | 9/2006 |
| WO | 00/78971 | 12/2000 |
| WO | 00/78972 | 12/2000 |
| WO | 01/15676 | 3/2001 |
| WO | 2005/067904 | 7/2005 |

OTHER PUBLICATIONS

International Search Report issued Mar. 25, 2008 in the International (PCT) Application of which the present application is the U.S. National Stage.
M. B. Neuworth et al., "Synthesis and Hypocholesterolemic Activity of Alkylidenedithio Bisphenols", Journal of Medicinal Chemistry, vol. 13, No. 4, pp. 722-725, 1970.
Y. Mizushima, "Today's Therapeutic Agents Commentary and Manual '99", pp. 429-433, 1999 (with English summary).
S. J. T. Mao et al., "Attenuation of Atherosclerosis in a Modified Strain of Hypercholesterolemic Watanabe Rabbits with Use of a Probucol Analogue (MDL 29;311) That Does Not Lower Serum Cholesterol", Arteriosclerosis and Thrombosis, vol. 11, No. 5, pp. 1266-1275, 1991.
C. F. Higgins et al., "ABC TRANSPORTERS: From Microorganisms to Man", Ann. Rev. Cell Biol., vol. 8, pp. 67-113, 1992.
L. R. McLean et al., "Interactions of MDL 29,311 and Probucol Metabolites with Cholesteryl Esters", Lipids, vol. 29, No. 12, pp. 819-823, 1994.
P. Metzner, "No. 404—Organic Sulfur Compounds. XLIV—Thiocetones α, β-ethyleniques: reaction with the diazoalkanes", Bulletin de la Societe Chimique de France, 7-8(Pt. 2), pp. 2297-2300, 1973 (with English abstract).
Supplementary European Search Report (in the English language) dated Apr. 8, 2010, issued in corresponding European Application No. 07 83 2277.

* cited by examiner

*Primary Examiner* — Rei-tsang Shiao
(74) *Attorney, Agent, or Firm* — Wenderoth, Lind & Ponack, L.L.P.

(57) ABSTRACT

A novel spiroquinone derivative having a high ABCA1 stabilization effect and being useful for prophylactic and/or therapeutic agents for various diseases developing hypo-high density lipoproteinemia is obtained. The novel spiroquinone derivative is a compound represented by the following formula:

[Formula 1]

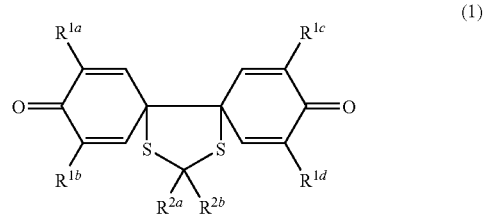

wherein $R^{1a}$, $R^{1b}$, $R^{1c}$ and $R^{1d}$ each represents a hydrogen atom, a halogen atom, an alkyl group which may have a substituent, or an alkoxy group which may have a substituent, and $R^{2a}$ and $R^{2b}$ each represents a hydrogen atom, or an alkyl group which may have a substituent (e.g., a carboxyl group, an alkoxycarbonyl group, a carbamoyl group, and an N-substituted carbamoyl group), the groups $R^{2a}$ and $R^{2b}$ may bond together to form a hydrocarbon ring with an adjacent carbon atom, provided that compounds in which all of the groups $R^{1a}$, $R^{1b}$, $R^{1c}$ and $R^{1d}$ are t-butyl groups, and both of the groups $R^{2a}$ and $R^{2b}$ are hydrogen atoms or both of the groups $R^{2a}$ and $R^{2b}$ are methyl groups are excluded; or a pharmacologically acceptable salt thereof.

11 Claims, No Drawings

SPIROQUINONE COMPOUND AND PHARMACEUTICAL COMPOSITION

This application is a U.S. national stage of International Application No. PCT/JP2007/072547 filed Nov. 21, 2007.

TECHNICAL FIELD

The present invention relates to a novel spiroquinone compound or a pharmacologically acceptable salt thereof (hereinafter, sometimes a spiroquinone derivative is used as a general term for the spiroquinone compound or the pharmacologically acceptable salt thereof and a pharmaceutical composition containing the spiroquinone derivative.

BACKGROUND ART

ABCA1 (ATP-binding cassette transport 1) is a protein present in mainly cell membranes in cells of a variety of organs including liver, intestinum tenue, placenta, and adrenal gland. Moreover, the ABCA1 is a member of ABC protein family which probably participates in membrane transport of various substances such as a lipid, an amino acid, a vitamin, and a sugar (see Non-patent Document 1).

Further, ABCA1 is an essential protein for a reaction that produces a high-density lipoprotein (HDL) from lipids of cells, and is also a rate-determining factor (or a rate-limiting factor) of the HDL production. The HDL production by ABCA1 is also a main releasing route of cell cholesterol including HDL. HDL is a lipid-protein complex particle produced by an action of a helical apolipoprotein (e.g., apoprotein A-I (apoAI)) that is mainly synthesized in and secreted from liver and intestinum tenue epithelial cells and protein ABCA1 present in cell membranes. HDL removes excess cholesterol from peripheral tissues in blood and transports the excess cholesterol back to the liver, which is called "reverse cholesterol transport", and has an extremely important role in the lipid metabolism, and HDL cholesterol is sometimes called "good cholesterol".

Moreover, the level of HDL in blood is measured as an index of the concentration of HDL cholesterol. In general, a subject having a blood HDL cholesterol level of less than 40 mg/dl is diagnosed as "hypo-high density lipoproteinemia". This hypo-high density lipoproteinemia is often regarded as a risk factor for various diseases including arteriosclerosis, hyperlipemia, brain infarction, stroke, obesity, diabetes, and metabolic syndrome. In addition, the hypo-high density lipoproteinemia is also observed in various genetic diseases including Tangier disease. However, useful prophylactic or therapeutic agents for preventing or treating hypo-high density lipoproteinemia by acting on HDL itself have not been found, and appearance of such agents has been desired.

As described above, ABCA1 is a rate-determining factor of HDL production. Therefore, for the development of prophylactic and/or therapeutic agents for hypo-high density lipoproteinemia, various approaches to the increase of HDL production by ABCA1 have been conducted. For example, attempts to increase ABCA1 expression and activity by directly introducing a gene encoding ABCA1 to a host cell for the purpose of increasing cholesterol efflux and raising HDL concentration (see Patent Documents 1 and 2) and attempts to increase transcription and translation of ABCA1 gene by a specific substance for the purpose of modulating HDL cholesterol and triglyceride levels and enhance ABCA1 expression and activity (see Patent Document 3) are disclosed. Moreover, findings on inclusion of cholesterol into cells by a bisphenol-based probucol compound have also been obtained (see Non-patent Document 2). However, these documents do not specifically state on ABCA1 expression and prophylactic and/or therapeutic effects of hypo-high density lipoproteinemia by a probucol spiroquinone compound or a bisphenol-based probucol compound.

WO2005/67904 (Patent Document 4) discloses a prophylactic and/or therapeutic agent for hypo-high density lipoproteinemia, and the agent contains probucol spiroquinone, probucol diphenoquinone, and/or probucol bisphenol which are metabolites of probucol which is a therapeutic agent for hyperlipemia. However, it is difficult to say that these probucol compounds induce fully stable and continuous ABCA1 expression and prophylactic and/or therapeutic effects of hypo-high density lipoproteinemia. Incidentally, "Bulletin de la Societe Chimique de France" (France), 7-8(Pt. 2), 1973, p 2297-2300 (Non-patent Document 3) discloses that a dithiolane-1,3 compound having a spiro ring skeleton is obtained by a reaction of a cycloalkene-2-thione (such as cyclohexene-2-thione) and $R'(R'')CN_2$.

[Patent Document 1] International Publication No. WO00/78971

[Patent Document 2] International Publication No. WO00/78972

[Patent Document 3] International Publication No. WO01/15676

[Patent Document 4] International Publication No. WO05/67904

[Non-patent Document 1] "Annual Review of Cell Biology" (United States), 8, 1992, p 67-113

[Non-patent Document 2] "Lipids" (United States), 29(12), 1994, p 819-823

[Non-patent Document 3] "Bulletin de la Societe Chimique de France" (France), 7-8(Pt. 2), 1973, p 2297-2300

DISCLOSURE OF THE INVENTION

Problems to be Solved by the Invention

It is an object of the present invention to provide a novel spiroquinone derivative having an excellent ABCA1 stabilization action and a process for producing the spiroquinone derivative, as well as a pharmaceutical composition containing the spiroquinone derivative and an ABCA1 stabilizer containing the spiroquinone derivative.

Another object of the present invention is to provide an improving agent for hypo-high density lipoproteinemia, the agent which can improve HDL production effectively and is effective for the prophylaxis or treatment of hypo-high density lipoproteinemia.

It is a further object of the present invention to provide an effectively prophylactic (preventive) or therapeutic (treating) agent for various diseases attributable to hypo-high density lipoproteinemia (for example, arteriosclerosis, brain infarction, stroke, hyperlipemia, metabolic syndrome, cirrhosis, myeloma, diabetes, obesity, chronic renal insufficiency, thyroid dysfunction, or a chronic inflammatory enteropathy (Crohn's disease, ulcerative colitis)).

Means to Solve the Problems

The inventors of the present invention made intensive studies to achieve the above objects and finally found that a specific novel spiroquinone derivative has an excellent ABCA1 stabilization action, that this stabilization action depends on an inhibitive effect of ABCA1 degradation and is attributable to stable and continuous increase of ABCA1 level in cells, and that the ABCA1 stabilization raises HDL production, thereby being effective for preventing or treating hypo-high density lipoproteinemia and various diseases caused by hypo-high density lipoproteinemia. The present invention was accomplished based on the above findings.

That is, the spiroquinone derivative of the present invention is a compound (a spiroquinone compound) represented by the following formula (1) or a pharmacologically acceptable salt thereof. Incidentally, respective positions in the structure of the spiroquinone compound represented by the following formula (1) are given individual numbers.

[Formula 1]

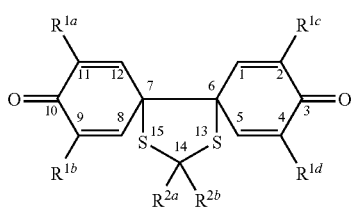
(1)

In the formula, $R^{1a}$, $R^{1b}$, $R^{1c}$ and $R^{1d}$ are the same or different and each represents a hydrogen atom, a halogen atom, an alkyl group which may have a substituent, or an alkoxy group which may have a substituent, and $R^{2a}$ and $R^{2b}$ are the same or different and each represents a hydrogen atom, a carboxyl group, an alkoxycarbonyl group, a carbamoyl group, an N-substituted carbamoyl group, an alkyl group which may have a substituent, an aryl group which may have a substituent, or an aralkyl group which may have a substituent, the groups $R^{2a}$ and $R^{2b}$ may bond together to form a hydrocarbon ring with an adjacent carbon atom, and the hydrocarbon ring may have a substituent, provided that compounds in which all of the groups $R^{1a}$, $R^{1b}$, $R^{1c}$ and $R^{1d}$ are t-butyl groups, and both of the groups $R^{2a}$ and $R^{2b}$ are hydrogen atoms or both of the groups $R^{2a}$ and $R^{2b}$ are methyl groups are excluded.

Incidentally, in the compound represented by the formula (1) or a salt thereof, the carbonyl group of 4-position of the benzene ring may form a hydroxyl group. That is, the spiroquinone derivative of the present invention includes not only a ketone form but also an enol form.

The groups $R^{1a}$, $R^{1b}$, $R^{1c}$ and $R^{1d}$ may be the same or different and each may represent a linear (or straight) or branched $C_{1-6}$alkyl group (for example, a branched $C_{3-6}$alkyl group) which may have a substituent or a linear (or straight) or branched $C_{1-6}$alkoxy group (for example, a branched $C_{3-6}$alkoxy group) which may have a substituent.

The substituent of the alkyl group represented by the groups $R^{2a}$ and $R^{2b}$ may be at least one substituent selected from the group consisting of a halogen atom, a hydroxyl group, an alkoxy group, a haloalkoxy group, an acyl group, an acyloxy group, a carboxyl group, an alkoxycarbonyl group, a carbamoyl group, an N-substituted carbamoyl group, a cyano group, and a nitro group. The hydrocarbon ring which is formed by the bond of the groups $R^{2a}$ and $R^{2b}$ and the adjacent carbon atom may be a 4- to 8-membered saturated or unsaturated hydrocarbon ring. The hydrocarbon ring may have at least one substituent selected from the group consisting of a halogen atom, a hydroxyl group, an alkoxy group, a haloalkoxy group, an acyloxy group, a carboxyl group, an alkoxycarbonyl group, a carboxyalkyl group, an alkoxycarbonylalkyl group, a carbamoyl group, a carbamoylalkyl group, an N-substituted carbamoyl group, an N-substituted carbamoylalkyl group, a cyano group, and a nitro group. The groups $R^{2a}$ and $R^{2b}$ may be the same or different and each may represent a hydrogen atom; a carboxyl group; a $C_{1-6}$alkoxy-carbonyl group (e.g., a $C_{1-4}$alkoxy-carbonyl group); a carbamoyl group; an N-substituted carbamoyl group; a $C_{6-12}$aryl group which may have a $C_{1-4}$alkyl group (e.g., a $C_{6-10}$aryl group which may have a $C_{1-2}$alkyl group); a $C_{6-12}$aryl group which may have a $C_{1-4}$alkoxy group (e.g., a $C_{6-10}$aryl group which may have a $C_{1-2}$alkoxy group); a $C_{6-12}$aryl-$C_{1-4}$alkyl group which may have a $C_{1-4}$alkyl group; a $C_{6-12}$aryl-$C_{1-4}$alkyl group which may have a $C_{1-4}$alkoxy group; a $C_{1-6}$alkyl group (e.g., a $C_{1-4}$alkyl group); a $C_{1-6}$alkyl group having a halogen atom (e.g., a $C_{1-4}$alkyl group having a halogen atom); a carboxy$C_{1-6}$alkyl group (e.g., a carboxy-$C_{1-4}$alkyl group); a $C_{1-6}$alkyl group having a $C_{1-6}$alkoxy-carbonyl group (e.g., a $C_{1-4}$alkoxy-carbonyl-$C_{1-4}$alkyl group); a carbamoyl$C_{1-6}$alkyl group (e.g., a carbamoyl$C_{1-4}$alkyl group); or an N-substituted carbamoyl$C_{1-6}$alkyl group (e.g., an N-substituted carbamoyl$C_{1-4}$alkyl group); or the groups $R^{2a}$ and $R^{2b}$ may bond together to form a 4- to 6-membered saturated or unsaturated hydrocarbon ring with the adjacent carbon atom.

In the production process of the present invention, the compound represented by the formula (1) or the pharmacologically acceptable salt thereof (the spiroquinone derivative) is produced by treating a dithioacetal compound represented by the following formula (2) with an oxidant.

[Formula 2]

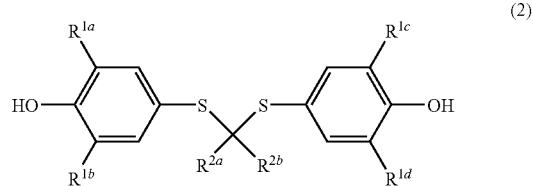
(2)

In the formula, $R^{1a}$, $R^{1b}$, $R^{1c}$, $R^{1d}$, $R^{2a}$ and $R^{2b}$ have the same meanings as defined above.

The dithioacetal compound represented by the formula (2) may be produced by allowing a mercaptophenol compound represented by the following formula (3a) and/or (3b) to react with a carbonyl compound represented by the following formula (4) in the presence of an acid.

[Formula 3]

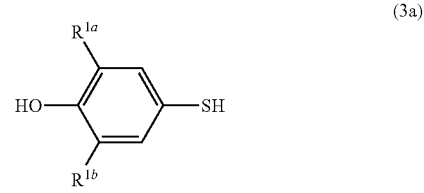
(3a)

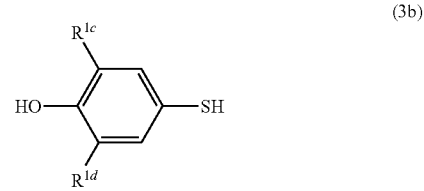
(3b)

-continued

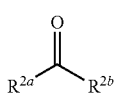

(4)

In the formula, $R^{1a}$, $R^{1b}$, $R^{1c}$, $R^{1d}$, $R^{2a}$ and $R^{2b}$ have the same meanings as defined above.

Incidentally, in the formulae (2), (3a) and (3b), the hydroxyl group of 4-position of the benzene ring may form a carbonyl group. That is, the dithioacetal compound represented by the formula (2) and the mercaptophenol compounds represented by the formulae (3a) and (3b) may be an enol form or a ketone form.

The pharmaceutical composition of the present invention contains the spiroquinone derivative (the spiroquinone compound or the pharmacologically acceptable salt thereof) and a carrier. Moreover, the present invention includes an ABCA1 stabilizer (or an ABCA1-stabilizing agent) containing the spiroquinone derivative as an effective ingredient, an improving agent for hypo-high density lipoproteinemia, the agent containing the spiroquinone derivative as an effective ingredient.

Further, the present invention includes a prophylactic and/or therapeutic agent for preventing and/or treating a disease selected from the group consisting of arteriosclerosis, brain infarction, stroke, hyperlipemia, metabolic syndrome, cirrhosis, myeloma, diabetes, obesity, chronic renal insufficiency, thyroid dysfunction, and a chronic inflammatory enteropathy (Crohn's disease, ulcerative colitis), the agent containing the spiroquinone derivative as an effective ingredient.

Effects of the Invention

The spiroquinone derivative of the present invention has a specific structure and an excellent ABCA1 stabilization action. Therefore, the spiroquinone derivative is useful for an ABCA1 stabilizer or is used in combination with a carrier for a pharmaceutical composition. Moreover, the spiroquinone derivative having an excellent ABCA1 stabilization action can effectively improve HDL production. Accordingly, the spiroquinone derivative is effective for the prophylaxis or treatment of hypo-high density lipoproteinemia and useful for an improving agent for hypo-high density lipoproteinemia. Further, the spiroquinone derivative has excellent prophylactic or therapeutic effect(s) on various diseases attributable to hypo-high density lipoproteinemia (for example, arteriosclerosis, brain infarction, stroke, hyperlipemia, metabolic syndrome, cirrhosis, myeloma, diabetes, obesity, chronic renal insufficiency, thyroid dysfunction, and a chronic inflammatory enteropathy (Crohn's disease, ulcerative colitis)).

DETAILED DESCRIPTION OF THE INVENTION

Spiroquinone Derivative

The spiroquinone derivative of the present invention includes a compound (spiroquinone compound) represented by the formula (1) or a pharmacologically acceptable salt thereof (for example, a medically or pharmaceutically acceptable salt).

The halogen atom represented by each of the groups $R^{1a}$, $R^{1b}$, $R^{1c}$ and $R^{1d}$ in the formula (1) may include fluorine atom, chlorine atom, bromine atom, iodine atom, and others.

Moreover, the alkyl group represented by each of the groups $R^{1a}$, $R^{1b}$, $R^{1c}$ and $R^{1d}$ may include, for example, a $C_{1-10}$alkyl group such as methyl, ethyl, propyl, isopropyl, butyl, s-butyl, isobutyl, t-butyl, pentyl, isopentyl, neopentyl, hexyl, isohexyl, neohexyl, heptyl, isoheptyl, octyl, isooctyl, or decyl group.

The substituent of the alkyl group represented by each of the groups $R^{1a}$, $R^{1b}$, $R^{1c}$ and $R^{1d}$ may include at least one substituent selected from the group consisting of a halogen atom (for example, fluorine, chlorine, bromine, or iodine atom, preferably fluorine, chlorine, or bromine atom), a hydroxyl group, an alkoxy group [for example, a $C_{1-10}$alkoxy group such as methoxy group, ethoxy group, n-propoxy group, isopropoxy group, n-butoxy group, isobutoxy group, s-butoxy group, or t-butoxy group, preferably a $C_{1-6}$alkoxy group, and more preferably a lower alkoxy group (e.g., a $C_{1-4}$alkoxy group)], a haloalkoxy group [for example, a fluoroalkoxy group corresponding to the above-mentioned alkoxy group (e.g., a fluoromethoxy group (such as trifluoromethoxy group), a fluoroethoxy group (such as 2,2,2-trifluoroethoxy group or perfluoroethoxy group), and a perfluoropropoxy group), and a chloroalkoxy group, a bromoalkoxy group and an iodoalkoxy group, each corresponding to the fluoroalkoxy group], an acyl group (for example, a $C_{1-10}$alkylcarbonyl group such as formyl, acetyl, propionyl, or butyryl group, preferably a $C_{1-6}$alkyl-carbonyl group, and more preferably a $C_{1-4}$alkyl-carbonyl group, a $C_{3-10}$cycloalkyl-carbonyl group such as cyclohexylcarbonyl group, a $C_{6-10}$arylcarbonyl group such as benzoyl group, and a $C_{6-10}$aryl-$C_{1-4}$alkylcarbonyl group such as benzylcarbonyl group), an acyloxy group (for example, a $C_{2-10}$acyloxy group such as acetoxy group, propionyloxy group, or butyryloxy group, preferably a $C_{2-6}$acyloxy group, and more preferably a $C_{2-4}$acyloxy group), a carboxyl group, an alkoxycarbonyl group [for example, a $C_{1-10}$alkoxy-carbonyl group such as methoxycarbonyl group, ethoxycarbonyl group, n-propoxycarbonyl group, isopropoxycarbonyl group, n-butoxycarbonyl group, isobutoxycarbonyl group, s-butoxycarbonyl group, or t-butoxycarbonyl group, preferably a $C_{1-6}$alkoxycarbonyl group, and a lower alkoxycarbonyl group (e.g., a $C_{1-4}$alkoxy-carbonyl group)], a carbamoyl group, an N-substituted carbamoyl group [for example, the above-exemplified substituted carbamoyl group, e.g., an N-mono$C_{1-6}$alkyl-carbamoyl group, an N—$C_{1-6}$acyl-carbamoyl group, an N,N-di$C_{1-6}$alkylcarbamoyl group, and an N,N-di$C_{1-6}$acyl-carbamoyl group], a cyano group, and a nitro group.

The alkoxy group represented by each of the groups $R^{1a}$, $R^{1b}$, $R^{1c}$ and $R^{1d}$ may include, for example, a $C_{1-10}$alkoxy group such as methoxy, ethoxy, propoxy, isopropoxy, butoxy, s-butoxy, isobutoxy, t-butoxy, pentyloxy, isopentyloxy, neopentyloxy, hexyloxy, isohexyloxy, neohexyloxy, heptyloxy, isoheptyloxy, octyloxy, isooctyloxy, or decyloxy group.

The substituent of the alkoxy group represented by each of the groups $R^{1a}$, $R^{1b}$, $R^{1c}$ and $R^{1d}$ may include the same substituent as exemplified in the paragraph of the substituent of the alkyl group.

Each of the groups $R^{1a}$, $R^{1b}$, $R^{1c}$ and $R^{1d}$ may be a hydrogen atom and is usually an alkyl group or an alkoxy group (for example, a $C_{1-6}$alkyl group or a $C_{1-6}$alkoxy group). The alkyl group and alkoxy group may be in a form of a linear chain (or a straight chain) and is usually in a form of a branched chain. The preferred alkyl group includes a branched alkyl group (or an alkyl group having a branched chain), for example, a branched $C_{3-6}$alkyl group such as isopropyl, s-butyl, isobutyl, t-butyl, isopentyl, neopentyl, isohexyl, or neohexyl group. Moreover, the preferred alkoxy group may include a branched chain alkoxy group, for example, a branched chain $C_{3-6}$alkoxy group such as isopropoxy, s-butoxy, isobutoxy, t-butoxy, isopentyloxy, neopentyloxy, isohexyloxy, or neohexyloxy group.

In the formula (1), the species of the groups $R^{1a}$, $R^{1b}$, $R^{1c}$ and $R^{1d}$ may be independently different from each other. Among these groups, there are usually the following relationships: $R^{1a}=R^{1c}$ and $R^{1b}=R^{1d}$ or $R^{1a}=R^{1b}$ and $R^{1c}=R^{1d}$. In particular, there is usually the following relationship: $R^{1a}=R^{1c}=R^{1b}=R^{1d}$. Further, the species of the groups $R^{1a}$, $R^{1b}$, $R^{1c}$ and $R^{1d}$ are usually the same alkyl group (for example, t-butyl group) or the same alkoxy group (for example, t-butoxy group).

In the formula (1), each of the groups $R^{2a}$ and $R^{2b}$ includes a hydrogen atom, a carboxyl group, a group derived from a carboxyl group (an alkoxycarbonyl group, a carbamoyl group, and an N-substituted carbamoyl group), an alkyl group which may have a substituent, an aryl group which may have a substituent, or an aralkyl group which may have a substituent. The species of the groups $R^{2a}$ and $R^{2b}$ may be the same or different from each other.

The alkoxycarbonyl group may include, for example, a $C_{1-10}$alkoxy-carbonyl group such as methoxycarbonyl group, ethoxycarbonyl group, n-propoxycarbonyl group, isopropoxycarbonyl group, n-butoxycarbonyl group, isobutoxycarbonyl group, s-butoxycarbonyl group, or t-butoxycarbonyl group, preferably a $C_{1-6}$alkoxy-carbonyl group, and a lower alkoxycarbonyl group (e.g., a $C_{1-4}$alkoxy-carbonyl group).

The N-substituted carbamoyl group may include an N-mono-substituted carbamoyl group [for example, an N-mono$C_{1-6}$alkylcarbamoyl group (such as N-methylcarbamoyl, N-ethylcarbamoyl, or N-butylcarbamoyl group), an N-mono$C_{6-10}$arylcarbamoyl group (such as N-phenylcarbamoyl group), and an N—$C_{1-6}$acylcarbamoyl group (such as N-formylcarbamoyl, N-acetylcarbamoyl, or N-propionylcarbamoyl group)]; and an N,N-di$C_{1-6}$acylcarbamoyl group [for example, a N,N-di$C_{1-6}$alkylcarbamoyl group (such as N,N-dimethylcarbamoyl or N,N-diethylcarbamoyl group), and an N,N-diacetylcarbamoyl group].

The alkyl group represented by each of the groups $R^{2a}$ and $R^{2b}$ may include an unsubstituted alkyl group [for example, a $C_{1-10}$alkyl group such as methyl group, ethyl group, propyl group, isopropyl group, n-butyl group, isobutyl group, s-butyl group, t-butyl group, or pentyl group, preferably a $C_{1-6}$alkyl group, and more preferably a lower alkyl group (e.g., a $C_{1-4}$alkyl group)] and a substituted alkyl group corresponding to the unsubstituted alkyl group.

The substituent of the alkyl group represented by each of the groups $R^{2a}$ and $R^{2b}$ may include the same substituent as exemplified in the paragraph of the substituent of the alkyl group represented by each of the groups $R^{1a}$, $R^{1b}$, $R^{1c}$ and $R^{1d}$.

The aryl group which may have a substituent may include, for example, a $C_{6-12}$aryl group (such as phenyl or naphthyl group) and the above-mentioned $C_{6-12}$aryl group having a substituent. The substituent may include, for example, a halogen atom (e.g., fluorine, chlorine, and bromine atoms), an alkyl group (e.g., a linear or branched $C_{1-6}$alkyl group such as methyl, ethyl, propyl, isopropyl, or a butyl group), an alkoxy group (e.g., a linear or branched $C_{1-6}$alkoxy group such as methoxy, ethoxy, a propoxy, or a butoxy group), a carboxyl group, an alkoxycarbonyl group (e.g., the above-mentioned $C_{1-4}$alkoxy-carbonyl group), a cyano group, and a nitro group. The aryl group which may have a substituent may be a $C_{6-12}$aryl group which may have a $C_{1-4}$alkyl group (e.g., a $C_{6-10}$aryl group which may have a $C_{1-2}$alkyl group) or a $C_{6-12}$aryl group which may have a $C_{1-4}$alkoxy group (e.g., a $C_{6-10}$aryl group which may have a $C_{1-2}$alkoxy group).

The aralkyl group which may have a substituent may include, for example, an aralkyl group which may have the same substituent as described in the paragraph of the aryl group. Such an aralkyl group may be, for example, a $C_{6-12}$aryl-$C_{1-4}$alkyl group which may have a $C_{1-4}$alkyl group (e.g., a $C_{6-10}$aryl-$C_{1-2}$alkyl group which may have a $C_{1-2}$alkyl group) and a $C_{6-12}$aryl-$C_{1-4}$alkyl group which may have a $C_{1-4}$alkoxy group (e.g., a $C_{6-10}$aryl-$C_{1-2}$alkyl group which may have a $C_{1-2}$alkoxy group).

The number of substituents on the alkyl group represented by each of the groups $R^{2a}$ and $R^{2b}$ may suitably be selected depending on the number of carbon atoms of the alkyl group, and others. The number of substituents may be one, or two or more (for example, 2 to 6, preferably 2 to 4, and more preferably 2 or 3). When the alkyl group represented by each of the groups $R^{2a}$ and $R^{2b}$ has a plurality of substituents, the species of the substituents may be the same or different from each other.

Incidentally, the compound of the present invention dose not encompass a compound in which all of the groups $R^{1a}$, $R^{1b}$, $R^{1c}$ and $R^{1d}$ are t-butyl groups and both of the groups $R^{2a}$ and $R^{2d}$ are hydrogen atoms in the formula (1), and a compound in which all of the groups $R^{1a}$, $R^{1b}$, $R^{1c}$ and $R^{1d}$ are t-butyl groups and both of the groups $R^{2a}$ and $R^{2b}$ are methyl groups in the formula (1). For example, in the formula (1), when all of the groups $R^{1a}$, $R^{1b}$, $R^{1c}$ and $R^{1d}$ are t-butyl groups and $R^{2a}$ is hydrogen atom, $R^{2b}$ is an alkyl group which may have a substituent; when all of the groups $R^{1a}$, $R^{1b}$, $R^{1c}$ and $R^{1d}$ are t-butyl groups and $R^{2a}$ is methyl group, $R^{2b}$ is hydrogen atom or an alkyl group which has two or more carbon atoms and which may have a substituent.

Moreover, in the formula (1), the groups $R^{2a}$ and $R^{2b}$ may bond together to form a hydrocarbon ring with an adjacent carbon atom. The hydrocarbon ring may have a substituent. The hydrocarbon ring site or moiety formed by the bond of the groups $R^{2a}$ and $R^{2b}$ and the adjacent carbon atom is represented by the following formula (1a):

[Formula 4]

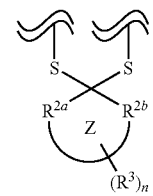

(1a)

wherein Z represents a hydrocarbon ring formed by the bond of $R^{2a}$ and $R^{2b}$ and the adjacent carbon atom, $R^3$ represents a substituent of the hydrocarbon ring Z, and "n" represents the number of the substituent $R^3$ and denotes an integer of 0 to 3.

The hydrocarbon ring (Z) may include, for example, a saturated hydrocarbon ring such as cyclobutane ring, cyclopentane ring, cyclohexane ring, cycloheptane ring, or cyclooctane ring; and an unsaturated hydrocarbon ring (an unsaturated alicyclic hydrocarbon ring) such as cyclobutene ring, cyclopentene ring, cyclohexene ring, cyclohexadiene ring, cycloheptene ring, or cyclooctene ring. The number of members constituting the hydrocarbon ring Z is not particularly limited to a specific one. The hydrocarbon ring Z may be, for example, a 4- to 8-membered ring, preferably a 4- to 7-membered ring (e.g., a 4- to 6-membered ring), and more preferably a 5- or 6-membered ring.

The hydrocarbon ring (Z) may have a substituent ($R^3$). The substituent ($R^3$) may include a substituent as exemplified in the paragraph of the substituent of the alkyl group represented by each of the groups $R^{2a}$ and $R^{2b}$, a carboxyalkyl group [for example, a carboxy$C_{1-10}$alkyl group such as carboxymethyl group, carboxyethyl group, carboxypropyl group, carboxyisopropyl group, carboxy-n-butyl group, carboxyisobutyl group, carboxy-s-butyl group, or carboxypentyl group, preferably a carboxy$C_{1-6}$alkyl group, and more preferably a carboxy lower alkyl group (e.g., a carboxy$C_{1-4}$alkyl group)], and an alkoxycarbonylalkyl group (e.g., a $C_{1-10}$alkoxy-carbonyl-$C_{1-6}$alkyl group such as methoxycarbonylmethyl, ethoxycarbonylmethyl, ethoxycarbonylethyl, butoxycarbonylethyl, or butoxycarbonylbutyl group, preferably a $C_{1-6}$alkoxy-carbonyl-$C_{1-4}$alkyl group, and a $C_{1-4}$alkoxy-carbonyl-$C_{1-2}$alkyl group). The number (n) of substituents may be preferably an integer of 0 to 2 and more preferably 0 or 1. Incidentally, when the hydrocarbon ring (Z) has a plurality of substituents, the species of the substituents ($R^3$) may be the same or different from each other.

Among the groups $R^{2a}$ and $R^{2b}$, the preferred group includes a hydrogen atom, a carboxyl group, an alkoxycarbonyl group (a $C_{1-6}$alkoxy-carbonyl group, particularly a $C_{1-4}$alkoxy-carbonyl group), a carbamoyl group, an N-substituted carbamoyl group (e.g., an N,N-dialkylcarbamoyl group and an N,N-diacylcarbamoyl group), an aryl group (e.g., a $C_{6-12}$aryl group), a $C_{6-12}$aryl group which may have a $C_{1-4}$alkyl group, a $C_{6-12}$aryl group which may have a $C_{1-4}$alkoxy group, a $C_{6-12}$aryl-$C_{1-4}$alkyl group which may have a $C_{1-4}$alkyl group, a $C_{6-12}$aryl-$C_{1-4}$alkyl group which may have a $C_{1-4}$alkoxy group, an alkyl group (e.g., a $C_{1-6}$alkyl group, particularly a $C_{1-4}$alkyl group), an alkyl group having a halogen atom (e.g., a halo$C_{1-6}$alkyl group, particularly a halo$C_{1-4}$alkyl group), a carboxyalkyl group (e.g., a carboxy$C_{1-6}$alkyl group, particularly a carboxy$C_{1-4}$alkyl group), an alkoxycarbonylalkyl group (e.g., a $C_{1-6}$alkoxy-carbonyl-$C_{1-6}$alkyl group, particularly a $C_{1-4}$alkoxy-carbonyl-$C_{1-4}$ alkyl group), a carbamoylalkyl group (e.g., a carbamoyl$C_{1-6}$alkyl group, particularly a carbamoyl$C_{1-4}$alkyl group), an N-substituted carbamoylalkyl group (e.g., an N-substituted carbamoyl$C_{1-6}$alkyl group, particularly an N-substituted carbamoyl$C_{1-4}$alkyl group), and others. Moreover, it is also preferable that the groups $R^{2a}$ and $R^{2b}$ bond together to form a 4- to 6-membered saturated or unsaturated hydrocarbon ring.

Concrete examples of the compound of the formula (1) include the following compounds:

(i) compounds in which $R^{2a}$ is hydrogen atom and $R^{2b}$ is an alkyl group:

a 14-$C_{1-6}$alkyl-2,4,9,11-tetrakis($C_{1-6}$alkyl)-13,15-dithiadispiro[5.0.5.3]pentadeca-1,4,8,11-tetraene-3,10-dione such as 14-methyl-2,4,9,11-tetrakis(t-butyl)-13,15-dithiadispiro[5.0.5.3]pentadeca-1,4,8,11-tetraene-3,10-dione;

(ii) compounds in which both of groups $R^{2a}$ and $R^{2b}$ are alkyl groups (provided that a compound in which all of the groups $R^{1a}$, $R^{1b}$, $R^{1c}$ and $R^{1d}$ are t-butyl groups and both of the groups $R^{2a}$ and $R^{2b}$ are methyl groups is excluded):

(ii-1) a 14-methyl-14-$C_{2-6}$alkyl-2,4,9,11-tetrakis($C_{1-6}$alkyl)-13,15-dithiadispiro[5.0.5.3]pentadeca-1,4,8,11-tetraene-3,10-dione such as 14,14-dimethyl-2,4,9,11-tetrakis(isopropyl)-13,15-dithiadispiro[5.0.5.3]pentadeca-1,4,8,11-tetraene-3,10-dione, 14-ethyl-14-methyl-2,4,9,11-tetrakis(t-butyl)-13,15-dithiadispiro[5.0.5.3]pentadeca-1,4,8,11-tetraene-3,10-dione, 14-methyl-2,4,9,11-tetrakis(t-butyl)-14-n-propyl-13,15-dithiadispiro[5.0.5.3]pentadeca-1,4,8,11-tetraene-3,10-dione, or 14-n-butyl-14-methyl-2,4,9,11-tetrakis(t-butyl)-13,15-dithiadispiro[5.0.5.3]pentadeca-1,4,8,11-tetraene-3,10-dione;

(ii-2) a 14,14-di$C_{2-6}$alkyl-2,4,9,11-tetrakis($C_{1-6}$alkyl)-13,15-dithiadispiro[5.0.5.3]pentadeca-1,4,8,11-tetraene-3,10-dione such as 14,14-diethyl-2,4,9,11-tetrakis(t-butyl)-13,15-dithiadispiro[5.0.5.3]pentadeca-1,4,8,11-tetraene-3,10-dione, 14-ethyl-2,4,9,11-tetrakis(t-butyl)-14-n-propyl-13,15-dithiadispiro[5.0.5.3]pentadeca-1,4,8,11-tetraene-3,10-dione, or 2,4,9,11-tetrakis(t-butyl)-14,14-di-n-propyl-13,15-dithiadispiro[5.0.5.3]pentadeca-1,4,8,11-tetraene-3,10-dione;

(iii) compounds in which $R^{2a}$ is an alkyl group and $R^{2b}$ is hydroxyl group, a carboxyl group, an alkoxycarbonyl group, a carbamoyl group, or an N-substituted carbamoyl group; or an alkyl group having a carboxyl group, an alkoxycarbonyl group, a carbamoyl group, or an N-substituted carbamoyl group as a substituent:

(iii-1) a 14-hydroxy$C_{1-4}$alkyl-14-$C_{1-6}$alkyl-2,4,9,11-tetrakis($C_{1-6}$alkyl)-13,15-dithiadispiro[5.0.5.3]pentadeca-1,4,8,11-tetraene-3,10-dione such as 14-hydroxymethyl-14-methyl-2,4,9,11-tetrakis(t-butyl)-13,15-dithiadispiro[5.0.5.3]pentadeca-1,4,8,11-tetraene-3,10-dione;

(iii-2) a 14-carboxy-14-$C_{1-16}$alkyl-2,4,9,11-tetrakis($C_{1-6}$ alkyl)-13,15-dithiadispiro[5.0.5.3]pentadeca-1,4,8,11-tetraene-3,10-dione; a 14-$C_{1-4}$alkoxy-carbonyl-14-$C_{1-6}$alkyl-2,4,9,11-tetrakis($C_{1-6}$alkyl)-13,15-dithiadispiro[5.0.5.3]pentadeca-1,4,8,11-tetraene-3,10-dione;

(iii-3) a 14-carbamoyl-14-$C_{1-6}$alkyl-2,4,9,11-tetrakis($C_{1-6}$ alkyl)-13,15-dithiadispiro[5.0.5.3]pentadeca-1,4,8,11-tetraene-3,10-dione; a 14-(N-mono$C_{1-6}$alkyl- or N,N-di$C_{1-6}$ alkyl-carbamoyl)-14-$C_{1-6}$alkyl-2,4,9,11-tetrakis($C_{1-6}$alkyl))-13,15-dithiadispiro[5.0.5.3]pentadeca-1,4,8,11-tetraene-3,10-dione; a 14-(N-mono$C_{1-6}$alkylcarbonyl- or N,N-di$C_{1-6}$ alkylcarbonyl-carbamoyl)-14-$C_{1-6}$alkyl-2,4,9,11-tetrakis ($C_{1-6}$alkyl)-13,15-dithiadispiro[5.0.5.3]pentadeca-1,4,8,11-tetraene-3,10-dione;

(iii-4) a 14-carboxy$C_{1-4}$alkyl- or 14-$C_{1-4}$alkoxy-carbonyl$C_{1-4}$alkyl-14-$C_{1-6}$alkyl-2,4,9,11-tetrakis($C_{1-6}$alkyl)-13,15-dithiadispiro[5.0.5.3]pentadeca-1,4,8,11-tetraene-3,10-dione such as 14-carboxyethyl-14-methyl-2,4,9,11-tetrakis(t-butyl)-13,15-dithiadispiro[5.0.5.3]pentadeca-1,4,8,11-tetraene-3,10-dione, or 14-methoxycarbonylmethyl-14-methyl-2,4,9,11-tetrakis(t-butyl)-13,15-dithiadispiro[5.0.5.3]pentadeca-1,4,8,11-tetraene-3,10-dione; and (iii-5) a 14-carbamoyl$C_{1-4}$alkyl- or 14-$C_{1-4}$alkoxy-carbonyl$C_{1-4}$alkyl-14-$C_{1-6}$alkyl-2,4,9,11-tetrakis($C_{1-6}$alkyl)-13,15-dithiadispiro[5.0.5.3]pentadeca-1,4,8,11-tetraene-3,10-dione; a 14-(N-substituted carbamoyl)$C_{1-4}$alkyl-14-$C_{1-6}$ alkyl-2,4,9,11-tetrakis($C_{1-6}$alkyl)-13,15-dithiadispiro [5.0.5.3]pentadeca-1,4,8,11-tetraene-3,10-dione; and (iv) compounds in which the groups $R^{2a}$ and $R^{2b}$ bond together to form a saturated or unsaturated $C_{4-6}$hydrocarbon ring with an adjacent carbon atom:

compounds in which the groups $R^{1a}$, $R^{1b}$, $R^{1c}$ and $R^{1d}$ are $C_{1-6}$alkyl groups and the groups $R^{2a}$ and $R^{2b}$ bond together to form a $C_{4-8}$cycloalkane ring with an adjacent carbon atom, such as 9,11,15,17-tetrakis(t-butyl)-6,19-dithiadispiro[4.1.5$^7$.0.5$^{13}$.1$^5$]nonadeca-8,11,14,17-tetraene-10,16-dione, or 8,10,14,16-tetrakis(t-butyl)-5,18-dithiadispiro[3.1.5$^6$.0.5$^{12}$.1$^4$]octadeca-7,10,13,16-tetraene-9,15-dione.

The spiroquinone derivative also includes a pharmacologically acceptable salt of the compound of the formula (1). Such a salt may include a salt of the compound of the formula (1) with an acid or base. The acid for forming the salt may include an inorganic acid (for example, hydrochloric acid, sulfuric acid, nitric acid, and phosphoric acid) and an organic acid (for example, an organic carboxylic acid such as acetic acid, trichloroacetic acid, trifluoroacetic acid, succinic acid, fumaric acid, or maleic acid, a hydroxycarboxylic acid such as lactic acid, malic acid, tartaric acid, or citric acid, a sulfonic acid such as methanesulfonic acid or toluenesulfonic acid). The base may suitably be selected depending on the species of the compound of the formula (1) and may include, for example, an inorganic base (e.g., ammonia, an alkali metal hydroxide such as sodium hydroxide or potassium hydroxide, an alkali metal carbonate, an alkaline earth metal hydroxide such as calcium hydroxide or magnesium hydroxide, and an alkaline earth metal carbonate), and an organic base (e.g., an alkylamine, an alkanolamine, and a polyamine such as an alkylenediamine). These acids or bases may be used alone or in combination.

Incidentally, the compound of the formula (1) may be in the form of an anhydride or a hydrate or may be in the form of a solvate (e.g., an organic solvent solvate such as ethanol solvate). Moreover, the compound of the formula (1) may be a prodrug in which functional group(s) of the compound (e.g., $R^{1a}$, $R^{1b}$, $R^{1c}$, $R^{1d}$, $R^{2a}$ and $R^{2b}$) is modified and is capable of expressing an activity in a living body. The prodrug may include, for example, a compound which can be converted into the compound of the formula (1) by metabolism such as hydrolysis, oxidation, reduction, or transesterification (for example, an ester form, ether form, alcohol form, amide form, or amine derivative of the compound of the formula (1)). Incidentally, the compound of the formula (1) includes not only a hydrate or solvate of the compound of the formula (1) but also a matter isolated as a polymorphic crystalline substance. Moreover, the spiroquinone derivative of the present invention also includes a tautomer, optically active substance having an asymmetric carbon atom (e.g., a (R) form, a (S) form, and a diastereomer), racemic modification, or mixture thereof, of the compound of the formula (1) or a salt thereof.

(Production Process)

The spiroquinone derivative may be produced by various processes. For example, the spiroquinone derivative may be produced according to the following reaction steps:

[Formula 5]

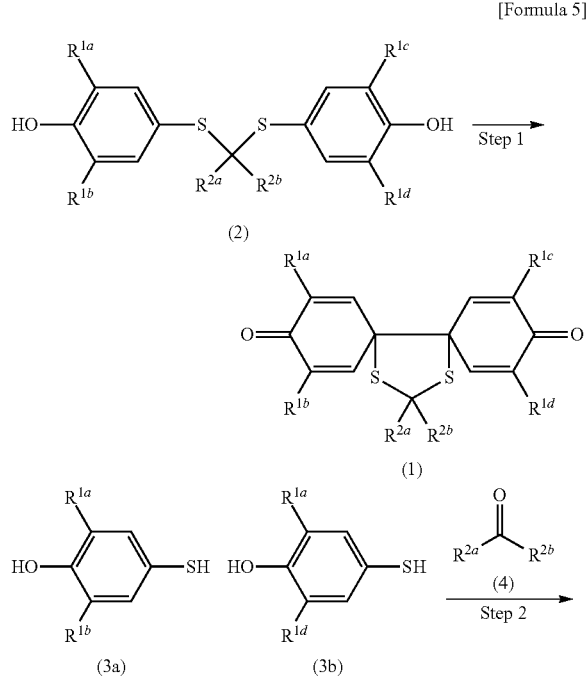

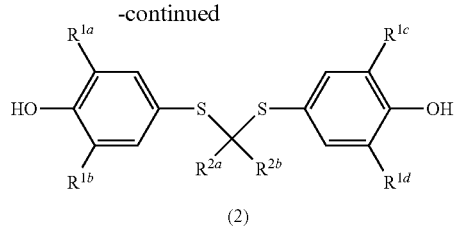

(2)

wherein the groups $R^{1a}$, $R^{1b}$, $R^{1c}$, $R^{1d}$, $R^{2a}$ and $R^{2b}$ have the same meanings as defined above.

Specifically, as indicated in the step 1, the spiroquinone compound represented by the formula (1) or a salt thereof can be obtained by an intramolecular coupling reaction of the dithioacetal compound represented by the formula (2). Moreover, the dithioacetal compound represented by the formula (2) can be obtained, as indicated in the step 2, by allowing the mercaptophenol compound represented by the formula (3a) and/or (3b) (e.g., 2,6-di-t-butyl-4-mercaptophenol) to react with the carbonyl compound represented by the formula (4). Incidentally, if necessary, the salt of the spiroquinone compound may be produced by subjecting the spiroquinone compound to a conventional salt-forming reaction. Moreover, the salt may be formed in a suitable stage of the reaction. For example, a raw material which is represented by the formula (2), (3a), (3b) or (4) and forms a salt may be used for the reaction to produce a salt of the spiroquinone compound (1), or the obtained spiroquinone compound (1) may be allowed to react with an acid or base to form a salt.

(Step 1)

In the step 1, the spiroquinone compound (1) or a salt thereof is produced by forming a spiro ring through the intramolecular coupling reaction of the dithioacetal compound (2).

A compound corresponding to the spiroquinone compound (1) may be used as the substrate dithioacetal compound (2). Such a compound may be used in the form of a hydrate or salt. Incidentally, it is not necessary that the dithioacetal compound (2) be synthesized according to the above-mentioned reaction steps. A commercially available product may be used as the dithioacetal compound (2). Moreover, the dithioacetal compound (2) may be synthesized by a conventional manner or a modified manner thereof, and others.

The above-mentioned coupling reaction can be carried out in the presence of an oxidant. A metal oxide is usually employed as the oxidant. The metal oxide may include, for example, an alkaline earth metal oxide such as selenium dioxide; a transition metal oxide such as cerium oxide, manganese dioxide, ruthenium oxide, osmium oxide, copper oxide, or silver oxide; an oxide of a metal of the group 14 of the Periodic Table of Elements, such as lead oxide; and an oxide of a metal of the group 15 of the Periodic Table of Elements, such as bismuth oxide. Among these metal oxides, particularly, an oxide of a metal of the group 7 of the Periodic Table of Elements, such as manganese dioxide, and others are preferred. Incidentally, the oxidants may be used alone or in combination. Moreover, the metal oxide may be used in combination with another oxidant (for example, a conventional oxidant other than the metal oxide, such as molecular oxygen, a peroxide, or chromic acid).

The proportion of the oxidant relative to 1 mol of the substrate dithioacetal compound (2) is about 0.5 to 20 mol, preferably about 1 to 15 mol, and more preferably about 2 to 10 mol.

The reaction of the step 1 can be carried out in the presence or absence of a solvent. When the reaction is carried out in the presence of a solvent, the solvent may include a solvent inactive to the reaction, for example, a hydrocarbon (an aliphatic hydrocarbon such as hexane, an alicyclic hydrocarbon such as cyclohexane, and an aromatic hydrocarbon such as toluene), a halogenated hydrocarbon (e.g., chloroform, dichloromethane, and trichloroethane), an alcohol (e.g., methanol, ethanol, and isopropanol), an ether (a chain ether such as diethyl ether or diisopropyl ether, and a cyclic ether such as dioxane or tetrahydrofuran), a nitrile (e.g., acetonitrile, propionitrile, and benzonitrile), a cellosolve, a carboxylic acid (e.g., acetic acid and propionic acid), an ester (e.g., ethyl acetate), a ketone (e.g., acetone and methyl ethyl ketone), an amide (e.g., N,N-dimethylformamide and N,N-dimethylacetamide), a sulfoxide (e.g., dimethyl sulfoxide), and a sulfolane. These solvents may be used alone or as a mixed solvent in combination. Among these solvents, a hydrocarbon, a halogenated hydrocarbon, and others are preferred.

The reaction temperature may be selected, for example, from a wide range of 0 to 200° C. depending on the species of the groups $R^{1a}$, $R^{1b}$, $R^{1c}$, $R^{1d}$, $R^{2a}$ and $R^{2b}$, the species of the solvent, and others. The reaction temperature may be preferably about 10 to 180° C. and more preferably about a room temperature (about 20 to 25° C.) to 160° C. Moreover, the reaction can be carried out under an oxidation atmosphere (e.g., an oxygen-containing gas such as air) or an inactive gas atmosphere (e.g., nitrogen, helium, or argon gas). The reaction may be conducted under a reduced pressure or an applied pressure or may be conducted under an atmospheric pressure.

The obtainable compound (1) or a salt thereof may be separated or purified by a conventional separation or purification (or isolation) method, for example, filtration, redistribution, salting-out, distillation, solvent removal, precipitation (e.g., precipitation by salt formation), crystallization, recrystallization, decantation, extraction, drying, washing, chromatography, and a combination thereof.

(Step 2)

In the step 2, the dithioacetal compound (2) is synthesized by allowing the mercaptophenol compound represented by the formula (3a) and/or (3b) (e.g., 2,6-di-t-butyl-4-mercaptophenol) to react with the carbonyl compound represented by the formula (4).

The mercaptophenol compound represented by the formula (3a) and/or (3b) (for example, 2,6-di-t-butyl-4-mercaptophenol) may use either a commercially available product or a compound produced by a conventional manner or a modified manner thereof. The mercaptophenol compound represented by the formula (3a) and/or (3b) can be prepared by the conventional manner. For example, 2,6-di-t-butyl-4-mercaptophenol may be produced by allowing 3,5-bis-t-butyl-4-hydroxyphenylthiocyanate to react with water in the presence of triethylphosphine. The details of the production process of the mercaptophenol compound represented by the formula (3a) and/or (3b) (for example, 2,6-di-t-butyl-4-mercaptophenol) may be, for example, referred to Japanese Patent Application Laid-Open No. 218570/1986 (JP-61-218570A). Incidentally, regarding the mercaptophenol compound, the compound represented by the formula (3a) and the compound represented by the formula (3b) may be different from each other and is usually the same mercaptophenol compound (in these compounds, $R^{1a}=R^{1c}$ and $R^{1b}=R^{1d}$, particularly, $R^{1a}=R^{1c}=R^{1b}=R^{1d}$).

Incidentally, a compound corresponding to the dithioacetal compound (2) (and the spiroquinone derivative) can be used as the carbonyl compound (4). Either a commercially available product or a compound produced by a conventional manner or a modified manner thereof may be used. Moreover, the carbonyl compound (4) may be used in the form of a hydrate or salt.

The carbonyl compound (4) may include various compounds having at least one selected from the group consisting of carbonyl group and formyl group, for example, a ketone, an aldehyde, a keto alcohol, a keto carboxylic acid, and a keto carboxylic acid ester.

The ketone may include, for example, a $C_{1-10}$alkyl-$C_{1-10}$alkyl ketone such as acetone, 2-butanone, 2-pentanone, 3-pentanone, 2-hexanone, 3-hexanone, 3-heptanone, or isobutyl methyl ketone, a $C_{3-10}$cycloalkyl ketone such as cyclobutanone, cyclopentanone, cyclohexanone, methylcyclohexanone, or cyclooctanone, and an aromatic ketone such as acetophenone, propiophenone, butyrophenone, benzophenone, or dibenzyl ketone.

The aldehyde may include, for example, formaldehyde, an alkylaldehyde (e.g., a $C_{1-24}$alkylaldehyde such as acetaldehyde, propionaldehyde, butylaldehyde, isobutylaldehyde, valeraldehyde, capronaldehyde, or lauraldehyde), an arylaldehyde (e.g., an aromatic aldehyde such as benzaldehyde, tolualdehyde, or salicylaldehyde), a ketoaldehyde (e.g., an alkylcarbonylaldehyde such as methylglyoxal, an alkylcarbonylalkylaldehyde such as acetoacetaldehyde or levulinaldehyde, and an arylcarbonylaldehyde such as phenylglyoxal), and an aldehydic acid (glyoxylic acid, formylacetic acid, formylpropionic acid, phthalaldehydic acid).

The keto alcohol may include, for example, an alkylcarbonylalkyl alcohol (aliphatic ketol) such as acetol (hydroxyacetone), acetoin, acetoethyl alcohol (levulin alcohol), or diacetone alcohol, and an arylcarbonylalkyl alcohol (aromatic ketol) such as phenacyl alcohol or benzoin.

The keto carboxylic acid may include, for example, an α-keto acid [for example, an alkyl-carbonylcarboxylic acid such as pyruvic acid, 2-ketocaproic acid, 2-ketoenanthic acid, 2-ketocaprylic acid, 2-ketocapric acid, or 2-ketopalmitic acid (e.g., a $C_{1-24}$alkyl-carbonylcarboxylic acid, particularly a $C_{1-10}$alkyl-carbonylcarboxylic acid), an arylcarbonylcarboxylic acid such as benzoylformic acid (e.g., a $C_{6-10}$arylcarbonylcarboxylic acid), and an aralkylcarbonylcarboxylic acid such as phenylpyruvic acid (e.g., a $C_{6-10}$aryl-$C_{1-4}$alkyl-carbonylcarboxylic acid)], a β-keto acid [for example, an alkylcarbonylmethylcarboxylic acid such as acetoacetic acid, propionylacetic acid, 3-ketoenanthic acid, 3-ketocaprylic acid, 3-ketocapric acid, 3-ketopalmitic acid, ketolauric acid, ketopelargonic acid, ketobehenic acid, ketopentadecanoic acid, or ketoheneicosenoic acid (e.g., a $C_{1-24}$alkyl-carbonylmethylcarboxylic acid), and an arylcarbonylmethylcarboxylic acid such as benzoylacetic acid (e.g., a $C_{6-10}$aryl-carbonylmethylcarboxylic acid)], a γ-keto acid [for example, an alkylcarbonylethylcarboxylic acid such as levulinic acid (e.g., $C_{1-10}$alkyl-carbonylethylcarboxylic acid), and an arylcarbonylethylcarboxylic acid such as benzoylpropionic acid or benzylpyruvic acid (e.g., a $C_{6-10}$aryl-carbonylethylcarboxylic acid)], other keto acids (for example, an alkylcarbonylalkylcarboxylic acid (e.g., a $C_{1-10}$alkyl-carbonyl-$C_{3-10}$alkylcarboxylic acid), and an arylcarbonylalkylcarboxylic acid (e.g., a $C_{6-10}$aryl-carbonyl$C_{3-10}$alkylcarboxylic acid)), and a keto dicarboxylic acid (e.g., a carboxyalkylcarbonylcarboxylic acid such as 2-ketogluconic acid, 2-ketoglutaric acid, or ketopimelic acid, and a carboxyalkylcarbonylalkylcarboxylic acid such as 3-ketoglutaric acid).

The keto carboxylic acid ester may include an alkyl ester of the above-mentioned keto carboxylic acid, for example, a $C_{1-6}$alkyl ester of the above-mentioned keto carboxylic acid, such as methyl acetoacetate or ethyl acetoacetate.

Among these carbonyl compounds, a ketone (e.g., an alkyl ketone and a cycloalkyl ketone), an aldehyde (e.g., alkylaldehyde), a keto carboxylic acid or an ester thereof, and others are practically used.

The proportion of the carbonyl compound (4) may be selected from the range of about 0.1 to 10 mol relative to 1 mol of the total of the mercaptophenol compound represented by the formula (3a) and/or (3b) (e.g., 2,6-di-t-butyl-4-mercaptophenol). The proportion is usually about 0.1 to 5 mol (about 0.1 to 2 mol), preferably about 0.2 to 1.5 mol, and more preferably about 0.3 to 1 mol.

Moreover, the above-mentioned reaction is often carried out in the presence of an acid. The acid may be an organic acid (e.g., an organic carboxylic acid such as acetic acid, and an organic sulfonic acid such as methanesulfonic acid). It is usually preferable that the acid be an inorganic acid such as hydrochloric acid, sulfuric acid, nitric acid, or phosphoric acid. The acid to be used may also include, for example, a heteropoly acid and a cation-exchange resin, in addition to a Lewis acid (e.g., zinc chloride).

The proportion of the acid relative to 1 mol of the total of the mercaptophenol compound represented by the formula (3a) and/or (3b) (e.g., 2,6-di-t-butyl-4-mercaptophenol) is about 0.001 to 10 mol, preferably about 0.005 to 5 mol, and more preferably about 0.01 to 1 mol (e.g., about 0.05 to 0.5 mol).

The reaction may be carried out in the presence or absence of a solvent. Moreover, the acid and/or the carbonyl compound may be used as a solvent.

The solvent is not particularly limited to a specific one as long as the solvent is inactive to the reaction. For example, the solvent may include a hydrocarbon [e.g., an aliphatic hydrocarbon (such as hexane or heptane), an alicyclic hydrocarbon (such as cyclohexane), and an aromatic hydrocarbon (such as toluene)], a halogenated hydrocarbon (e.g., chloroform, dichloromethane, and trichloroethane), an alcohol (e.g., methanol, ethanol, and isopropanol), an ether [e.g., a chain ether (such as isopropyl ether, diethyl ether, or diisopropyl ether) and a cyclic ether (such as dioxane or tetrahydrofuran)], a cellosolve, a carboxylic acid (e.g., acetic acid and propionic acid), an ester (e.g., ethyl acetate), a ketone (e.g., acetone and methyl ethyl ketone), a nitrile (e.g., acetonitrile, propionitrile, and benzonitrile), an amide (e.g., N,N-dimethylformamide and N,N-dimethylacetamide), a sulfoxide (e.g., dimethyl sulfoxide), and a sulfolane. These solvents may be used alone or as a mixed solvent in combination. Among these solvents, a hydrocarbon, an alcohol, and an ether are preferably used.

The reaction temperature may suitably be selected from the range of about 0° C. to 100° C. and is preferably about 10 to 80° C., more preferably a room temperature (about 20 to 25° C.) to about 70° C. Moreover, the reaction can be carried out under an oxidation atmosphere (e.g., an oxygen-containing gas such as air) or an inactive gas atmosphere (e.g., nitrogen, helium, or argon gas). The reaction may be conducted under a reduced pressure or an applied pressure or may be conducted under an atmospheric pressure.

The compound (2) obtainable in this step may be used to the synthesis of the compound (1) in the step 1 after separation or purification by a conventional method or may be used to the synthesis of the compound (1) without any separation or purification.

Incidentally, not only the substituents $R^{1a}$, $R^{1b}$ $R^{1c}$, $R^{1d}$, $R^{2a}$ and $R^{2b}$ but also a substituent which the substituents $R^{1a}$, $R^{1b}$, $R^{1c}$ and $R^{1d}$, $R^{2a}$ and $R^{2b}$ further have may be introduced into a raw material compound represented by the formula (2), (3a), (3b) or (4) in advance. Alternatively, the compound (1) may be produced by preparing a precursor of the compound (1) from a raw material which does not have these substituents and introducing optional substituent(s) into the precursor with the use of a conventional method (e.g., oxidation, reduction, hydrolysis, and substitution reaction). For example, a keto carboxylic acid or a keto carboxylic acid ester may be used as the carbonyl compound (4) to give a compound in which $R^{2a}$ and $R^{2b}$ are a carboxyl group, an alkoxycarbonyl group, a carboxyalkyl group, or an alkoxycarbonylalkyl group. The alkoxycarbonyl group may be formed by using a keto carboxylic acid as the carbonyl compound (4) and esterifying the obtained carboxyl group. A carbamoyl group or an N-substituted carbamoyl group may be formed by using a keto carboxylic acid as the carbonyl compound (4), and subjecting a carboxyl group of the obtained spiroquinone compound or a salt thereof to a conventional method (for example, allowing the obtained spiroquinone compound or a salt thereof to react with ammonia, a primary or secondary amine, or an acylating agent). Moreover, among the above-mentioned substituents, a reactive group such as carboxyl group or hydroxyl group may be protected by a protective group, according to need, in a suitable stage of the reaction. The protective group may be removed in a suitable stage of the reaction.

(Application)

The spiroquinone derivative of the present invention has an excellent ABCA1 stabilization action, and the spiroquinone derivative is useful as an effective ingredient for an ABCA1 stabilizer. Incidentally, the ABCA1 stabilizer means an agent that stably and continuously expresses ABCA1 existing in cells (mainly cell membranes) of various organs including liver, intestinum tenue, placenta, and adrenal gland.

Moreover, the stabilization of ABCA1 means that ABCA1 exists in cells (particularly cell membranes) more stably and continuously when evaluated in the presence of the spiroquinone derivative, in comparison with when evaluated in the absence of the spiroquinone derivative. The stable and continuous existence of ABCA1 in cells accelerates HDL production reaction. There is a method which comprises increasing ABCA1 itself or inhibiting ABCA1 decomposition in order to allow ABCA1 exist in cells. The spiroquinone derivative of the present invention stably retains ABCA1 in cells by inhibition of ABCA1 decomposition rather than increase of ABCA1 itself and stabilizes ABCA1.

Thus, the spiroquinone derivative of the present invention has an excellent ABCA1 stabilization action and is useful as a prophylactic and/or therapeutic agent for a disease in which ABCA1 directly or indirectly participates (for example, an agent for improving hypo-high density lipoproteinemia and an agent for reducing LDL cholesterol), particularly, as a prophylactic and/or therapeutic agent for a disease caused by reduced ABCA1 expression (such as hypo-high density lipoproteinemia).

In particular, the above-mentioned spiroquinone derivative is useful as an effective ingredient for an agent for improving hypo-high density lipoproteinemia (a prophylactic and/or therapeutic agent). Incidentally, hypo-high density lipoproteinemia is observed in diseases such as arteriosclerosis, brain infarction, stroke, hyperlipemia, metabolic syndrome, cirrhosis, myeloma, diabetes, obesity, chronic renal insufficiency, thyroid dysfunction, and/or a chronic inflammatory enteropathy (e.g., Crohn's disease, ulcerative colitis). The above-mentioned spiroquinone derivative effectively improves hypo-high density lipoproteinemia in these diseases. The spiroquinone derivative may also be used as an effective ingredient for prophylactic and/or therapeutic agents for these diseases.

Further, the spiroquinone derivative of the present invention is also useful as a prophylactic and/or therapeutic agent for a coronary disease (including myocardial infarction, angina, silent ischemia, and coronary arteriosclerosis), arteriosclerosis, carotid sclerosis, a cerebrovascular disease (including brain infarction and stroke), arteriosclerosis obliterans, hyperlipemia, metabolic syndrome, fatty liver, cirrhosis, myeloma, diabetes, diabetes complication, a skin disease, xanthoma, a joint disease (arthropathy), a proliferative disease, peripheral arterial obstruction, an ischemic peripheral circulation disorder, obesity, cerebrotendinous xanthomatosis (CTX), chronic renal insufficiency, glomerular nephritis, hyperthyroidism, arteriosclerotic kidney, vascular thickening, vascular thickening after intervention (including percutaneous coronary arterioplasty, percutaneous coronary revascularization, stent placement, coronary angioscopy, intravascular ultrasound, and infusion thrombolytic therapy), vascular restenosis/reobstruction after bypass surgery, nephropathy or nephritis and pancreatitis strongly relating to hyperlipemia, hyperlipemia (including familial hypercholesterolemia and alimentary hyperlipemia), a chronic inflammatory enteropathy (including Crohn's disease and ulcerative colitis), intermittent claudication, deep-vein thrombosis, malarial encephalopathy, Alzheimer's disease, or a disease caused by wound or hypoplasia.

The spiroquinone derivative may be used alone as a pharmaceutical or may be used in combination with a carrier (for example, a pharmacologically or physiologically acceptable carrier) as a pharmaceutical composition (or preparation). Incidentally, the ABCA1 stabilizer, the improving agent for hypo-high density lipoproteinemia, and the prophylactic and/or therapeutic agent for the above-mentioned various diseases are not particularly limited to specific ones as long as the spiroquinone derivative is contained as an effective ingredient in these agents. These agents may contain the spiroquinone derivative alone or comprise a pharmaceutical composition containing the spiroquinone derivative and a carrier in the same manner as described the above.

In the pharmaceutical composition, the carrier may be selected suitably depending on the form (that is, dosage form) of the pharmaceutical composition (or preparation), the route of administration, the application, and others. The dosage form is not particularly limited to a specific one. The dosage form may be a solid preparation (for example, powdered preparations, powders, particles (e.g., granules and microfine particles or powders), spherical or spheroidal pills, pills, tablets, capsules, dry syrups, and suppositories), a semisolid preparation (for example, creams, ointments, gels, gumdrop-like preparations, film preparations, and sheet preparations), a liquid preparation (for example, solutions, suspensions, emulsions, syrup, elixir, lotions, and injectable solutions (or injections)), and others. Moreover, sprays or aerosols of the powdered preparations and/or the liquid preparation may be also included. Incidentally, the capsules may be a capsule having a liquid filled therein or a capsule having a solid preparation (such as granules) filled therein. Moreover, the preparation may be a lyophilized preparation. Further, an agent contained in the preparation of the present invention may be released at a controlled rate, that is, the preparation of the present invention may be a sustained release preparation or a rapid-release preparation. Incidentally, in aerosols utilized for an inhalant agent and others, a method for generating an aerosol is not particularly limited to a specific one. For example, a medically effective ingredient and a propellant (e.g., an alternative for chlorofluorocarbon) may be filled in a single hermetic container and sprayed. Moreover, a medically effective ingredient and a compressed gas (such as carbon dioxide or nitrogen gas) may be filled in separate containers and sprayed in the form of a nebulizer or an atomizer. Further, the preparation may be a preparation for oral administration or a preparation for parenteral administration (for example, a nosal preparation (or a collunarium), an inhalant preparation, and a preparation for transdermal administration). Furthermore, the preparation may be a preparation for topical administration (for example, solutions such as injectable solutions (e.g., aqueous injectable solutions and nonaqueous injectable solutions), suspensions, ointments, plasters and pressure sensitive adhesives, and cataplasms). The preparation of the present invention is practically a solid preparation (particularly, a preparation for oral administration).

The carrier may suitably be selected, depending on the route of administration and the application of the preparation, from components (for example, an excipient, a binder, a disintegrant, a lubricant, and a coating agent) listed in, for example, the Japanese Pharmacopoeia, (1) "Handbook of Pharmaceutical Excipients" (Maruzen Co., Ltd., 1989), (2) "Japanese Pharmaceutical Excipients Dictionary 2000" (Yakuji Nippo Ltd., issued on March, 2002), (3) "Japanese Pharmaceutical Excipients Dictionary 2005" (Yakuji Nippo Ltd., issued on May, 2005), (4) "Pharmaceuticals, Revised 2nd Edition" (Nankodo, Co., Ltd., 1997), and (5) "Japanese Pharmaceutical Excipients 2003 (Yakuji Nippo Ltd., August, 2003). For example, at least one carrier selected from the group consisting of an excipient, a binder, and a disintegrant is practically used as a carrier for the solid preparation. An additive such as a lipid may also be used therewith.

The excipient may include a saccharide or a sugar alcohol such as lactose, white soft sugar or refined sugar, glucose, sucrose, mannitol, sorbitol, or xylitol; a starch such as a corn starch; a polysaccharide such as a crystalline cellulose (including a microcrystalline cellulose); silicon dioxide or a silicate such as a light silicic anhydride or a synthetic aluminum silicate; and others. The binder may include a water-soluble starch such as a pregelatinized starch or a partially pregelatinized starch; a polysaccharide such as agar, gum acacia (or gum arabic), dextrin, sodium alginate, a tragacanth gum, a xanthan gum, a hyaluronic acid, or a sodium chondroitin sulfate; a synthetic polymer such as a polyvinylpyrrolidone, a polyvinyl alcohol, a carboxyvinyl polymer, a polyacrylic polymer, a polylactic acid, or a polyethylene glycol; a cellulose ether such as a methyl cellulose, an ethyl cellulose, a carboxymethyl cellulose, a carboxymethyl cellulose sodium, a hydroxyethyl cellulose, a hydroxypropyl cellulose, or a hydroxypropylmethyl cellulose; and others. The disintegrant may include calcium carbonate, a carboxymethyl cellulose or a salt thereof (e.g., a carmellose, a carmellose sodium, and a carmellose calcium), a polyvinylpyrrolidone (e.g., a polyvinylpyrrolidone and a crosslinked polyvinylpyrrolidone (crosslinked povidone)), a low-substituted hydroxypropyl cellulose, and others. These carriers may be used singly or in combination.

Incidentally, the coating agent may include, for example, a saccharide or a sugar, a cellulose derivative such as an ethyl cellulose or a hydroxymethyl cellulose, a polyoxyethylene glycol, a cellulose acetate phthalate, a hydroxypropylmethyl cellulose phthalate, a methyl methacrylate-(meth)acrylic acid copolymer, and eudragit (a copolymer of methacrylic acid and acrylic acid). The coating agent may be an enteric component (e.g., a cellulose phthalate, a hydroxypropylmethyl cellulose phthalate, and a methyl methacrylate-(meth)acrylic acid copolymer) or a gastric soluble component comprising a polymer containing a basic component such as a dialkylaminoalkyl(meth)acrylate (e.g., eudragit). Moreover, the preparation may be a capsule having such an enteric component or gastric soluble component as a capsule shell.

In the carrier of the liquid preparation, an oil-based carrier may include an oil derived from plants or animals (e.g., an oil derived from vegetables such as a jojoba oil, an olive oil, a palm oil, or a cotton seed oil; and an oil derived from animals such as squalene), a mineral oil (e.g., a liquid petrolatum and a silicone oil), and others. An aqueous carrier may include water (e.g., a purified water or a sterile water, a distilled water for injection), a physiological saline, a Ringer's solution, a glucose solution, a water-soluble organic solvent [for example, a lower aliphatic alcohol such as ethanol or isopropanol; a (poly)alkyleneglycol (e.g., ethylene glycol and a polyethylene glycol); and glycerin], dimethyl isosorbide, dimethylacetamide, and others. Moreover, the carrier of the semisolid preparation may be selected from the carrier of the solid preparation and/or that of the liquid preparation. Further, the carrier of the semisolid preparation may contain a lipid.

The lipid may include a wax (e.g., a bees wax, a carnauba wax, a lanolin, a paraffin, and a petrolatum), a higher (or long chain) fatty acid ester [e.g., an alkyl ester of a saturated or unsaturated fatty acid, and an ester of a fatty acid with a polyvalent alcohol (such as a poly$C_{2-4}$alkylene glycol, glycerin, or a polyglycerin) (e.g., a glyceride)], a hardened (or hydrogenated) oil, a higher alcohol (e.g., a saturated aliphatic alcohol such as stearyl alcohol and an unsaturated aliphatic alcohol such as oleyl alcohol), a higher fatty acid (e.g., linoleic acid, linoleic acid, stearic acid and oleic acid), a metallic soap (e.g., a metal salt of a fatty acid, such as a sodium salt of palm oil fatty acid or calcium stearate), and others.

In the preparation, known additives can be suitably used depending on an administration route, a dosage form, and others. Such an additive may include, for example, a lubricant (e.g., a talc, magnesium stearate, and a polyethylene glycol 6000), a disintegrant aid, an antioxidation agent or an antioxidant, an emulsifier (e.g., a variety of surfactants such as a nonionic surfactant), a dispersing agent, a suspending agent, a dissolving agent, a dissolution aid, a thickener (e.g., a water-soluble polymer such as a carboxyvinyl polymer, a polyvinyl alcohol, a carrageen, or a gelatin; and a cellulose ether such as a carboxymethyl cellulose), a pH adjusting agent or a buffer (e.g., a citric acid-sodium citrate buffer), a stabilizer, an antiseptic agent or a preservative (e.g., a paraben such as methyl paraben or butyl paraben), a fungicide or antibacterial agent (e.g., a benzoic acid compound such as sodium benzoate), an antistatic agent, a corrigent or a masking agent (e.g., sweetening agent), a coloring agent (e.g., a dye and a pigment such as colcothar), a deodorant or a perfume (e.g., an aromatic substance), an algefacient, an antifoaming agent, an isotonizing agent, and a soothing agent. These additives may be used singly or in combination.

For example, in the injectable solution, usually, the dissolving agent, the dissolution aid, the suspending agent, the buffer, the stabilizer, the preservative, and others may be used as the additive in practical cases. Incidentally, to powders for an injection, which are dissolved or suspended before administration, may be added conventional additive(s) used for powders for an injection.

Moreover, in a topically administering preparation such as an inhalant preparation or a transdermal absorption preparation, as the additive, usually, the dissolution aid, the stabilizer, the buffer, the suspending agent, the emulsifier, the preservative, and others may be practically used.

The pharmaceutical composition of the present invention may be prepared by using a carrier component in addition to an effective ingredient, and if necessary, an additive and the like, with a conventional preparation manner (for example, a production process described in Japanese Pharmacopoeia 15$^{th}$ edition or a process in accordance with the production process).

The spiroquinone derivative (including the ABCA1 stabilizer, the improving agent for hypo-high density lipoproteinemia, the prophylactic and/or therapeutic agent for various diseases, and the pharmaceutical composition) of the present invention is safely used for human beings and non-humans, usually mammals (e.g., human beings, mice, rats, rabbits, dogs, cats, bovines, horses, pigs, and monkeys).

The amount to be administered (or dose) of the spiroquinone derivative of the present invention may be suitably selected in accordance with the subject of administration, the age, body weight, sex, and condition (e.g., a performance status, a condition of a disease, and a presence of a complication) of the subject, the time (or period or schedule) of administration, the dosage form, the method (or route) of administration, and others. An effective amount of the spiroquinone derivative is usually administered. Moreover, the method of administration may be also selected in consideration for these items.

The amount to be administered (or dose) to human beings is, for example, in an oral administration, usually about 0.01 to 1,000 mg a day, preferably about 0.1 to 700 mg a day, and more preferably about 0.2 to 500 mg a day, as the basis for the amount to be used of the spiroquinone derivative. Moreover, in an injection, the amount to be administered to human beings is usually about 0.01 to 200 mg a day, preferably about 0.05 to 100 mg a day, and more preferably about 0.1 to 80 mg a day, as the basis for the amount to be used of the spiroquinone derivative. Further, in a topically administering agent, the amount to be administered to human beings is usually about 0.01 to 200 mg a day, preferably about 0.05 to 100 mg a day, and more preferably about 0.1 to 80 mg a day, as the basis for the amount to be used of the spiroquinone derivative. In order to determining the administration route and the amount to be administered (or dose) specifically, an optimum administration route and an optimum amount are designed with the condition (e.g., a performance status, a condition of a disease, and a presence of a complication), age, sex, and body weight of the patient, and the like.

For the purpose of an increased action, a reduced dosage, and a decreased side effect, the spiroquinone derivative of the present invention may be used in combination with one or more species of another agent (or drug or medicine) which does not adversely affect the effect(s) of the spiroquinone derivative. The agent which can be used in combination with the spiroquinone derivative may include a low molecular weight agent, a polypeptide, an antibody, a vaccine, and others. For example, the agent includes "a diabetic agent", "an agent for treating diabetic complication", "an antiobesity agent", "a hypertension-treating agent", "a hypolipidemic agent", "a diuretic agent", "an antithrombolic agent", and "an agent for Alzheimer's disease".

When the spiroquinone derivative of the present invention is used in combination with another agent, the route of administration is not particularly limited to a specific one. For example, a single preparation containing the spiroquinone derivative and another agent may be administered, or a first preparation containing the spiroquinone derivative and a second preparation containing another agent may be administered by the same administration route simultaneously or separately. Moreover, the first preparation and the second preparation may be administered by different administration routes simultaneously or separately.

INDUSTRIAL APPLICABILITY

The spiroquinone derivative of the present invention has an excellent ABCA1 stabilization action and is useful for an effective ingredient of an ABCA1 stabilizer, and additionally, an effective ingredient of an improving agent for hypo-high density lipoproteinemia in which ABCA1 participates (a prophylactic and/or therapeutic agent for hypo-high density lipoproteinemia). Moreover, the spiroquinone derivative of the present invention is also useful for prophylactic and/or therapeutic agents for various diseases developing hypo-high density lipoproteinemia, for example, a disease selected from arteriosclerosis, brain infarction, stroke, hyperlipemia, metabolic syndrome, cirrhosis, myeloma, diabetes, obesity, chronic renal insufficiency, thyroid dysfunction, and a chronic inflammatory enteropathy (e.g., Crohn's disease and ulcerative colitis).

EXAMPLES

Hereinafter, the following examples are intended to describe this invention in further detail and should by no means be interpreted as defining the scope of the invention.

Example 1

Synthesis of 14-carboxyethyl-14-methyl-2,4,9,11-tetrakis(t-butyl)-13,15-dithiadispiro[5.0.5.3]pentadeca-1,4,8,11-tetraene-3,10-dione

(i) Synthesis of 4,4-bis(3,5-di-t-butyl-4-hydroxyphenylthio)pentanoic acid

To a solution of 2,6-di-t-butyl-4-mercaptophenol (4.77 g, 20.0 mmol) in isopropyl ether (50 mL) was added levulinic acid (1.16 g, 10.0 mmol) and a catalytic amount of concentrated hydrochloric acid. The mixture was heated under reflux over 10 days. The solvent was distilled off from the reaction mixture, and the resulting residue was purified by a flash column chromatography (filler: manufactured by Kanto Kagaku, K.K., 60Nmesh40-100, developing solvent:n-hexane/ethyl acetate (volume ratio)=5/1 to 2/1) to give 4,4-bis(3,5-di-t-butyl-4-hydroxyphenylthio)pentanoic acid (yield 935 mg and 16%).

mp: 90-92° C.
$^1$H-NMR (CDCl$_3$) δ: 1.31 (3H, s), 1.43 (36H, s), 1.92-1.98 (2H, m), 2.76-2.82 (2H, m), 5.37 (2H, s), 7.41 (4H, s)

(ii) Synthesis of 14-carboxyethyl-14-methyl-2,4,9,11-tetrakis(t-butyl)-13,15-dithiadispiro[5.0.5.3]pentadeca-1,4,8,11-tetraene-3,10-dione In a mixture of hexane (10 mL) and dichloromethane (10 mL) was dissolved 4,4-bis(3,5-di-t-butyl-4-hydroxyphenylthio)pentanoic acid (600 mg, 1.04 mmol). Manganese dioxide (600 mg) was added to the resulting solution, and the resulting mixture was stirred overnight. The reaction mixture was filtered by using a celite, and the resulting filtrate was concentrated. The residue obtained by the concentration was purified by a flash column chromatography (filler: manufactured by Kanto Kagaku, K.K., 60Nmesh40-100, developing solvent:n-hexane/ethyl acetate (volume ratio)=1/0 to 2/1) to give an objective compound (yield 355 mg and 59%).

mp: 80-84° C.
$^1$H-NMR (CDCl$_3$) δ: 1.20 (36H, s), 2.00 (3H, s), 2.47-2.53 (2H, m), 2.66-2.72 (2H, m), 6.83-6.90 (4H, dd, J=2.7 Hz, 15.4 Hz)

Example 2

Synthesis of 14-methoxycarbonylmethyl-14-methyl-2,4,9,11-tetrakis(t-butyl)-13,15-dithiadispiro[5.0.5.3]pentadeca-1,4,8,11-tetraene-3,10-dione Methyl 3,3-bis(3,5-di-t-butyl-4-hydroxyphenylthio)butanoate was synthesized in the same manner as in Example 1 except for using 10.0 mmol of methyl acetoacetate instead of levulinic acid in the step (i) of Example 1.

$^1$H-NMR (CDCl$_3$) δ: 1.44 (36H, s), 1.57 (3H, s), 2.05 (2H, s), 3.70 (3H, s), 5.39 (2H, s), 7.46 (4H, s)

Further, an objective compound was synthesized in the same manner as in Example 1 except for using methyl 3,3-bis(3,5-di-t-butyl-4-hydroxyphenylthio)butanoate instead of 4,4-bis(3,5-di-t-butyl-4-hydroxyphenylthio)pentanoic acid as the raw material in the step (ii) of Example 1.

mp: 124-126° C.
$^1$H-NMR (CDCl$_3$) δ: 1.18 (18H, s), 1.20 (18H, s), 2.12 (3H, s), 3.26 (2H, s), 3.75 (3H, s), 6.80-6.89 (4H, dd, J=2.7 Hz, 21.1 Hz)

Example 3

Synthesis of 14-methyl-2,4,9,11-tetrakis(t-butyl)-13,15-dithiadispiro[5.0.5.3]pentadeca-1,4,8,11-tetraene-3,10-dione Bis(3,5-di-t-butyl-4-hydroxyphenylthio)ethane was synthesized in the same manner as in Example 1 except for using 10.0 mmol of acetaldehyde instead of levulinic acid in the step (i) of Example 1.

$^1$H-NMR (CDCl$_3$) δ: 1.43 (36H, s), 1.55 (3H, d, J=6.8 Hz), 4.24 (1H, q, J=6.8 Hz), 5.29 (2H, s), 7.37 (4H, s)

Further, an objective compound was synthesized in the same manner as in Example 1 except for using bis(3,5-di-t-butyl-4-hydroxyphenylthio)ethane instead of 4,4-bis(3,5-di-t-butyl-4-hydroxyphenylthio)pentanoic acid as the raw material in the step (ii) of Example 1.

mp: 131-133° C.
$^1$H-NMR (CDCl$_3$) δ: 1.19 (36H, s), 1.82 (3H, d, J=6.2 Hz), 5.09 (1H, q, J=6.2 Hz), 6.71-6.72 (2H, d, J=3.0 Hz), 6.81-6.82 (2H, d, J=3.0 Hz)

Example 4

Synthesis of 14-ethyl-14-methyl-2,4,9,11-tetrakis(t-butyl)-13,15-dithiadispiro[5.0.5.3]pentadeca-1,4,8,11-tetraene-3,10-dione In the same manner as in Example 1 except for using 10.0 mmol of 2-butanone instead of levulinic acid in the step (i) of Example 1, 2,2-bis(3,5-di-t-butyl-4-hydroxyphenylthio)butane was synthesized.

mp: 122-125° C.
$^1$H-NMR (CDCl$_3$) δ: 1.10 (3H, t, J=7.3 Hz), 1.31 (3H, s), 1.44 (36H, s), 1.65 (2H, q, J=7.3 Hz), 7.45 (4H, s)

Further, an objective compound was synthesized in the same manner as in Example 1 except for using 2,2-bis(3,5-di-t-butyl-4-hydroxyphenylthio)butane instead of 4,4-bis(3,5-di-t-butyl-4-hydroxyphenylthio)pentanoic acid as the raw material in the step (ii) of Example 1.

mp: 137-138° C.
$^1$H-NMR (CDCl$_3$) δ: 1.14-1.20 (39H, m), 1.97 (3H, s), 2.19 (2H, q, J=7.3 Hz), 6.84-6.85 (2H, d, J=3.0 Hz), 6.91-6.92 (2H, d, J=3.0 Hz)

Example 5

Synthesis of 14,14-diethyl-2,4,9,11-tetrakis(t-butyl)-13,15-dithiadispiro[5.0.5.3]pentadeca-1,4,8,11-tetraene-3,10-dione In the same manner as in Example 1 except for using 10.0 mmol of 3-pentanone instead of levulinic acid in the step (i) of Example 1, 3,3-bis(3,5-di-t-butyl-4-hydroxyphenylthio)pentane was synthesized.

mp: 145-150° C.
$^1$H-NMR (CDCl$_3$) δ: 1.06 (6H, t, J=7.3 Hz), 1.44-1.67 (40H, m), 5.33 (2H, s), 7.50 (4H, s)

Further, an objective compound was synthesized in the same manner as in Example 1 except for using 3,3-bis(3,5-di-t-butyl-4-hydroxyphenylthio)pentane instead of 4,4-bis(3,5-di-t-butyl-4-hydroxyphenylthio)pentanoic acid as the raw material in the step (ii) of Example 1.

mp: 136-139° C.
$^1$H-NMR (CDCl$_3$) δ: 1.08 (6H, t, J=7.3 Hz), 1.19 (36H, s), 2.23 (4H, q, J=7.3 Hz), 6.87 (4H, s)

Example 6

Synthesis of 14-methyl-2,4,9,11-tetrakis(t-butyl)-14-n-propyl-13,15-dithiadispiro[5.0.5.3]pentadeca-1,4,8,11-tetraene-3,10-dione In the same manner as in Example 1 except for using 10.0 mmol of 2-pentanone instead of levulinic acid in the step (i) of Example 1, 2,2-bis(3,5-di-t-butyl-4-hydroxyphenylthio)pentane was synthesized.

mp: 131-133° C.
$^1$H-NMR (CDCl$_3$) δ: 0.86 (3H, t, J=7.0 Hz), 1.21-1.71 (43H, m), 5.35 (2H, s), 7.44 (4H, s)

Further, an objective compound was synthesized in the same manner as in Example 1 except for using 2,2-bis(3,5-di-t-butyl-4-hydroxyphenylthio)pentane instead of 4,4-bis(3,5-di-t-butyl-4-hydroxyphenylthio)pentanoic acid as the raw material in the step (ii) of Example 1.

mp: 127-130° C.
$^1$H-NMR (CDCl$_3$) δ: 1.01 (3H, t, J=7.3 Hz), 1.19 (18H, s), 1.20 (18H, s), 1.51-1.61 (2H, m), 1.97 (3H, s), 2.11-2.17 (2H, m), 6.85-6.90 (4H, dd, J=3.0 Hz, 12.7 Hz)

Example 7

Synthesis of 14-ethyl-2,4,9,11-tetrakis(t-butyl)-14-n-propyl-13,15-dithiadispiro[5.0.5.3]pentadeca-1,4,8,11-tetraene-3,10-dione In the same manner as in Example 1 except for using 10.0 mmol of 3-hexanone instead of levulinic acid in the step (i) of Example 1, 3,3-bis(3,5-di-t-butyl-4-hydroxyphenylthio)hexane was synthesized.

mp: 156-158° C.
$^1$H-NMR (CDCl$_3$) δ: 0.81 (3H, t, J=7.3 Hz), 1.05 (3H, t, J=7.6 Hz), 1.34-1.67 (42H, m), 5.33 (2H, s), 7.49 (4H, s)

Further, an objective compound was synthesized in the same manner as in Example 1 except for using 3,3-bis(3,5-di-t-butyl-4-hydroxyphenylthio)hexane instead of 4,4-bis(3,5-di-t-butyl-4-hydroxyphenylthio)pentanoic acid as the raw material in the step (ii) of Example 1.

mp: 111-114° C.
$^1$H-NMR (CDCl$_3$) δ: 1.01 (3H, t, J=7.3 Hz), 1.09 (3H, t, J=7.3 Hz), 1.19 (18H, s), 1.20 (18H, s), 1.40-1.55 (2H, m), 2.14-2.25 (2H, m), 6.85-6.89 (4H, dd, J=3.0 Hz, 7.6 Hz)

Example 8

Synthesis of 14-n-butyl-14-methyl-2,4,9,11-tetrakis(t-butyl)-13,15-dithiadispiro[5.0.5.3]pentadeca-1,4,8,11-tetraene-3,10-dione In the same manner as in Example 1 except for using 10.0 mmol of 2-hexanone instead of levulinic acid in the step (i) of Example 1, 2,2-bis(3,5-di-t-butyl-4-hydroxyphenylthio)hexane was synthesized.

mp: 138-140° C.
$^1$H-NMR (CDCl$_3$) δ: 0.89 (3H, t, J=7.6 Hz), 1.32-1.59 (45H, m), 5.34 (2H, s), 7.44 (4H, s)

Further, an objective compound was synthesized in the same manner as in Example 1 except for using 2,2-bis(3,5-di-t-butyl-4-hydroxyphenylthio)hexane instead of 4,4-bis(3,5-di-t-butyl-4-hydroxyphenylthio)pentanoic acid as the raw material in the step (ii) of Example 1.

mp: 113-116° C.
$^1$H-NMR (CDCl$_3$) δ: 0.97 (3H, t, J=7.3 Hz), 1.19 (18H, s), 1.20 (18H, s), 1.37-1.57 (4H, m), 1.97 (3H, s), 2.12-2.18 (2H, m), 6.85-6.91 (4H, dd, J=3.0 Hz, 12.7 Hz)

Example 9

Synthesis of 2,4,9,11-tetrakis(t-butyl)-14,14-di(n-propyl)-13,15-dithiadispiro[5.0.5.3]pentadeca-1,4,8,11-tetraene-3,10-dione In the same manner as in Example 1 except for using 10.0 mmol of 4-heptanone instead of levulinic acid in the step (i) of Example 1, 4,4-bis(3,5-di-t-butyl-4-hydroxyphenylthio)heptane was synthesized.

mp: 159-161° C.
$^1$H-NMR (CDCl$_3$) δ: 0.80 (6H, t, J=7.3 Hz), 1.34-1.67 (44H, m), 5.34 (2H, s), 7.45 (4H, s)

Further, an objective compound was synthesized in the same manner as in Example 1 except for using 4,4-bis(3,5-di-t-butyl-4-hydroxyphenylthio)heptane instead of 4,4-bis(3,5-di-t-butyl-4-hydroxyphenylthio)pentanoic acid as the raw material in the step (ii) of Example 1.

mp: 117-118° C.
$^1$H-NMR (CDCl$_3$) δ: 1.00 (3H, t, J=7.3 Hz), 1.19 (36H, s), 1.43-1.52 (4H, m), 2.12-2.18 (4H, m), 6.87 (4H, s)

Example 10

Synthesis of 9,11,15,17-tetrakis(t-butyl)-6,19-dithiadispiro[4.1.5$^7$.0.5$^{13}$.1$^5$]nonadeca-8,11,14,17-tetraene-10,16-dione (i) Synthesis of bis(3,5-di-t-butyl-4-hydroxyphenylthio)cyclopentane To a solution of 2,6-di-t-butyl-4-mercaptophenol (600 mg, 1.04 mmol) in methanol (10 mL) was added cyclopentanone (1.5 mL) and a catalytic amount of concentrated hydrochloric acid. The mixture was heated and stirred at 60° C. overnight. The solvent was distilled off from the reaction mixture, and the resulting residue was purified by a flash column chromatography (filler: manufactured by Kanto Kagaku, K.K., 60Nmesh40-100, developing solvent:n-hexane/ethyl acetate (volume ratio)=1/0 to 100/1) to give bis(3,5-di-t-butyl-4-hydroxyphenylthio)cyclopentane (yield 485 mg and 67%).

mp: 138-143° C.

¹H-NMR (CDCl₃) δ: 1.44 (36H, s), 1.77-1.80 (8H, m), 5.32 (2H, s), 7.47 (4H, s)

(ii) Synthesis of 9,11,15,17-tetrakis(t-butyl)-13,15-dithiadispiro[4.1.5⁷.0.5¹³.1⁵]nonadeca 8,11,14,17-tetraene-10,16-dione Bis(3,5-di-t-butyl-4-hydroxyphenylthio)cyclopentane (400 mg, 0.73 mmol) obtained in the step (i) was dissolved in hexane (30 mL). Manganese dioxide (800 mg) was added to the resulting solution, and the mixture was stirred overnight. The reaction mixture was filtered by using a celite, and the resulting filtrate was concentrated. The residue obtained by the concentration was purified by a flash column chromatography (filler: manufactured by Kanto Kagaku, K.K., 60Nmesh40-100, developing solvent:n-hexane/ethyl acetate (volume ratio)=50/1) and then recrystallized from acetone and water to give an objective compound (yield 107 mg and 27%).

mp: 147-148° C.

¹H-NMR (CDCl₃) δ: 1.19 (36H, s), 1.78-1.83 (4H, m), 2.39-2.44 (4H, m), 6.87 (4H, s)

Example 11

Synthesis of 14,14-dimethyl-2,4,9,11-tetrakis(isopropyl)-13,15-dithiadispiro[5.0.5.3]pentadeca-1,4,8,11-tetraene-3,10-dione

(i) Synthesis of 2,2-bis(3,5-diisopropyl-4-hydroxyphenylthio)propane

To a solution of 2,6-diisopropyl-4-mercaptophenol (4.51 g, 21.5 mmol) in methanol (10 mL) was added acetone (5.0 mL) and a catalytic amount of concentrated hydrochloric acid. The mixture was heated under reflux overnight. The solvent was distilled off from the mixture. The resulting residue was purified by a silica gel column chromatography (manufactured by Yamazen Corporation, solvent: n-hexane/ethyl acetate (volume ratio)=5:1), and the solvent was distilled off. Thereafter, the resulting matter was crystallized from isopropyl ether to synthesize 2,2-bis(3,5-diisopropyl-4-hydroxyphenylthio)propane.

mp: 101-103° C.

¹H-NMR (CDCl₃) δ: 1.27 (24H, d, J=7.0 Hz), 1.44 (6H, s), 3.13 (4H, quin, J=7.0 Hz), 4.93 (2H, s), 0.32 (4H, s)

(ii) Synthesis of 14,14-dimethyl-2,4,9,11-tetrakis(isopropyl)-13,15-dithiadispiro[5.0.5.3]pentadeca-1,4,8,11-tetraene-3,10-dione To a mixed solution of 2,2-bis(3,5-diisopropyl-4-hydroxyphenylthio)propane (500 mg, 1.09 mmol) in dichloromethane (5 mL) and hexane (5 mL) was added manganese dioxide (500 mg). The mixture was stirred for 4 hours and then filtered by using a celite, and the resulting filtrate was concentrated. Hexane was added to the residue, and the mixture was stored in a refrigerator. The generated solid was separated by a filtration, washed with hexane, and then dried to synthesize an, objective compound.

mp: 98-100° C.

¹H-NMR (CDCl₃) δ: 1.00 (12H, d, J=7.0 Hz), 1.07 (12H, d, J=7.0 Hz), 2.02 (6H, s), 3.00 (4H, quin, J=7.0 Hz), 6.90 (4H, s)

Example 12

Synthesis of 14-hydroxymethyl-14-methyl-2,4,9,11-tetrakis(t-butyl)-13,15-dithiadispiro[5.0.5.3]pentadeca-1,4,8,11-tetraene-3,10-dione In the same manner as in Example 1 except for using hydroxyacetone (13.5 mmol) instead of levulinic acid in the step (i) of Example 1, 2,2-bis(3,5-di-t-butyl-4-hydroxyphenylthio)propanol was synthesized.

mp: 143-145° C.

¹H-NMR (CDCl₃) δ: 1.29 (3H, s), 1.44 (36H, s), 2.42 (1H, t, J=6.8 Hz), 3.46 (2H, d, J=6.8 Hz), 5.39 (2H, s), 7.40 (4H, s)

Further, an objective compound was synthesized in the same manner as in Example 1 except for using 2,2-bis(3,5-di-t-butyl-4-hydroxyphenylthio)propanol instead of 4,4-bis(3,5-di-t-butyl-4-hydroxyphenylthio)pentanoic acid as the raw material in the step (ii) of Example 1.

mp: 173-176° C.

¹H-NMR (CDCl₃) δ: 1.19 (18H, s), 1.21 (18H, s), 1.99 (3H, s), 2.37 (1H, t, J=7.0 Hz), 3.86 (2H, d, J=7.0 Hz), 6.85-6.86 (2H, d, J=3.0 Hz), 6.90-6.91 (2H, d, J=3.0 Hz)

Example 13

Synthesis of 8,10,14,16-tetrakis(t-butyl)-5,18-dithiadispiro[3.1.5⁶.0.5¹².1⁴]octadeca-7,10,13,16-tetraene-9,15-dione

(i) Synthesis of bis(3,5-di-t-butyl-4-hydroxyphenylthio)cyclobutane

To a solution of 2,6-di-t-butyl-4-mercaptophenol (2.00 g, 8.30 mmol) in methanol (10 mL) was added cyclobutanone (294 mg, 4.20 mmol) and a catalytic amount of concentrated hydrochloric acid. The mixture was heated under reflux for 6 hours. The solvent was distilled off from the mixture. The resulting residue was purified by a flash column chromatography to synthesize bis(3,5-di-t-butyl-4-hydroxyphenylthio)cyclobutane.

mp: 117-122° C.

¹H-NMR (CDCl₃) δ: 1.44 (36H, s), 1.95-2.03 (2H, m), 2.28 (4H, t, J=7.6 Hz), 5.30 (2H, s), 7.40 (4H, s)

(ii) Synthesis of 8,10,14,16-tetrakis(t-butyl)-5,18-dithiadispiro[3.1.5⁶.0.5¹².1⁴]octadeca-7,10,13,16-tetraene-9,15-dione To a solution of bis(3,5-di-t-butyl-4-hydroxyphenylthio)cyclobutane (360 mg, 0.68 mmol) in dichloromethane (50 mL) was added manganese dioxide (180 mg). The mixture was stirred for 3 hours and a half and then filtered by using a celite. Methanol was added to the resulting filtrate, and the filtrate was concentrated. The solid generated in process of the concentration was separated by a filtration, washed with methanol, and then dried to synthesize an objective compound.

mp: 154-156° C.

¹H-NMR (CDCl₃) δ: 1.18 (36H, s), 2.03 (2H, quin, J=7.8 Hz), 2.87 (4H, t, J=7.8 Hz), 6.76 (4H, s)

Example 14

Synthesis of 2,4,9,11-tetrakis(t-butyl)-13,20-dithiadispiro[5.0.5⁷.1¹⁴.5.1⁶]icosa-1,4,8,11-tetraene-3,10-dione)

(i) Synthesis of bis(3,5-di-t-butyl-4-hydroxyphenylthio)cyclohexane

To a solution of 2,6-di-t-butyl-4-mercaptophenol (3.00 g, 12.60 mmol) in methanol (10 mL) was added cyclohexanone (1.40 mL, 13.80 mmol) and a catalytic amount of concentrated hydrochloric acid. The mixture was stirred at a room temperature for 2 hours and then heated under reflux for one hour. The mixture was allowed to cool. Thereafter, the generated precipitate was separated by a filtration and dried to synthesize objective bis(3,5-di-t-butyl-4-hydroxyphenylthio)cyclohexane (yield 2.50 g and 71%).

mp: 171-174° C.
$^1$H-NMR (CDCl$_3$) δ: 1.35 (2H, br), 1.45 (36H, s), 1.64-1.68 (8H, m), 5.33 (2H, s), 7.51 (4H, s)

(ii) Synthesis of 2,4,9,11-tetrakis(t-butyl)-13,20-dithiadispiro[5.0.5$^7$.1$^{14}$.5.1$^6$]icosa-1,4,8,11-tetraene-3,10-dione To a solution of bis(3,5-di-t-butyl-4-hydroxyphenylthio)cyclohexane (1.00 g, 1.80 mmol) in dichloromethane (15 mL) was added manganese dioxide (312 mg). The mixture was stirred overnight and then filtered by using a celite. The resulting filtrate was concentrated. Hexane was added to the residue, and the mixture was stored in a refrigerator. The generated solid was separated by a filtration, washed with hexane, and then dried to give objective 2,4,9,11-tetrakis(t-butyl)-13,20-dithiadispiro[5.0.5$^7$.1$^{14}$.5.1$^6$]icosa-1,4,8,1'-tetraene-3,10-dione (yield 327 mg and 33%).

mp: 160-163° C.
$^1$H-NMR (CDCl$_3$) δ: 1.19 (36H, s), 1.42-1.45 (2H, m), 1.66-1.75 (4H, m), 2.20-2.24 (4H, m), 6.90-6.91 (2H, d, J=3.0 Hz)

Example 15

Synthesis of 2,4,9,11-tetrakis(t-butyl)-13,21-dithiadispiro[5.0.5$^7$.1$^{14}$.6.1$^6$]henicosa-1,4,8,11-tetraene-3,10-dione (i) Synthesis of bis(3,5-di-t-butyl-4-hydroxyphenylthio)cycloheptane To a solution of 2,6-di-t-butyl-4-mercaptophenol (3.00 g, 12.6 mmol) in methanol (10 mL) was added cycloheptanone (1.63 mL, 13.8 mmol) and a catalytic amount of concentrated hydrochloric acid. The mixture was stirred at a room temperature overnight. The generated precipitate was separated by a filtration and dried to give objective bis(3,5-di-t-butyl-4-hydroxyphenylthio)cycloheptane (yield 2.74 g and 76%).

mp: 144-146° C.
$^1$H-NMR (CDCl$_3$) δ: 1.45 (36H, s), 1.52 (8H, br), 1.77 (2H, br), 5.34 (2H, s), 7.52 (4H, s)

(ii) Synthesis of 2,4,9,11-tetrakis(t-butyl)-13,21-dithiadispiro[5.0.5$^7$.1$^{14}$.6.1$^6$]henicosa-1,4,8,11-tetraene-3,10-dione To a solution of bis(3,5-di-t-butyl-4-hydroxyphenylthio)cycloheptane (1.00 g, 1.80 mmol) in dichloromethane (15 mL) was added manganese dioxide (312 mg). The mixture was stirred overnight and then filtered by using a celite. The resulting filtrate was concentrated. Isopropyl ether and methanol were added to the residue, and the mixture was stored in a refrigerator. The generated solid was separated by a filtration, washed with isopropyl ether, and then dried to give objective 2,4,9,11-tetrakis(t-butyl)-13,21-dithiadispiro[5.0.5$^7$.1$^{14}$.6.1$^6$]henicosa-1,4,8,11-tetraene-3,10-dione (yield 1.05 g and 70%).

mp: 139-141° C.
$^1$H-NMR (CDCl$_3$) δ: 1.19 (36H, s), 1.57-1.74 (8H, m), 2.45-2.49 (4H, m), 6.87 (4H, s)

Hereinafter, procedures and results of pharmacological tests on validity and safety of the spiroquinone derivatives obtained in Examples will be explained.

Test Example 1

Increase of ABCA1 in THP-1 Cell

<Test Procedure>

THP-1 cells (human leukemia cell; manufactured by American Type Culture Collection) were cultured for 24 hours in 10% FBS-RPMI1640 culture medium (manufactured by Sigma) in the presence of PMA (phorbol myristate acetate; $3.2\times10^{-7}$ M; manufactured by Wako Pure Chemical Industries, Ltd.) to obtain differentiated macrophages. The resulting cells were washed with RPMI1640 (manufactured by Sigma) and then added to RPMI1640 culture medium (manufactured by Sigma) with BSA (manufactured by Sigma) having a concentration of 0.2%. The spiroquinone derivatives obtained in Examples 1, 6 and 10 was independently added to the culture medium. Each sample was cultured for 24 hours in the presence or absence of apoAI, and then the ABCA1 expression in the cells was assayed in accordance with the following method. Incidentally, the spiroquinone derivative was dissolved in 2-butabol, and the solution was added to the culture medium so that the final concentration of the spiroquinone derivative was 0.5%.

The cells were washed with PBS (phosphate buffered saline; manufactured by Sigma). The washed cells were collected in 0.5 mM Tris-HCl (pH 8.5) containing a protease inhibitor (manufactured by Sigma), stirred, and allowed to stand on ice for 15 minutes. The resulting cell suspension was centrifuged at 470×g for 5 minutes to precipitate nuclear fractions. Thereafter, the supernatant was centrifuged at 316,000×g for 30 minutes to precipitate membrane fractions. The membrane fractions (15 µg protein) were used to conduct SDS-PAGE and Immunoblotting. The obtained band of the ABCA1 protein was converted into digital data by using an image analysis software (manufactured by Microsoft Corporation, Photoshop). The relative ratio (%) of the ABCA1 expression level of the cells treated with the spiroquinone derivative to that of the cells treated with probucol spiroquinone was calculated to evaluate the ABCA1 expression activity of the test compounds.

<Results>

The results are shown in Table 1.

TABLE 1

| Test compounds | ABCA1 expression level (relative ratio %) |
|---|---|
| Probucol spiroquinone | 100 |
| Example 1 | 238 |
| Example 6 | 176 |
| Example 10 | 309 |

As shown in Table 1, the intracellular ABCA1 expression levels of THP-1 cells treated with the spiroquinone derivative of Examples 1, 6 or 10 were elevated about 1.7 to 3.0 times as compared with that of the cells treated with probucol spiroquinone.

Test Example 2

Acceleration of HDL Production Reaction

<Test Procedure>

The culture medium after 24-hour culture in the presence or absence of apoAI in Test Example 1 was used to examine cholesterol release into the culture medium by the apoA-1-dependent HDL-generating reaction.

Specifically, the culture medium was collected in a 1.5 ml tube and centrifuged at 316,000×g for 5 minutes, and the supernatant was transferred in a glass tube. To the supernatant was added a mixture of chloroform and methanol (volume ratio=2/1) (manufactured by Wako Pure Chemical Industries, Ltd.). The resulting mixture was stirred and further centrifuged at 1,300×g for 5 minutes. After the centrifugation, the resulting water layer was removed. Water was added to the remaining organic layer, and the mixture was stirred again and centrifuged at 1,300×g for 5 minutes. After the centrifugation, the resulting water layer was removed. The organic layer was evaporated to dryness, and cholesterol remaining in the glass tube was quantitatively determined according to an enzymatic method. The relative ratio (%) of the amount of cholesterol release as HDL from the cells treated with the spiroquinone derivative to that from the cells treated with probucol spiroquinone was calculated to evaluate the HDL cholesterol release from the cells treated with the test compounds.

<Results>

The results are shown in Table 2.

TABLE 2

| Test compounds | HDL cholesterol release (relative ratio %) |
|---|---|
| Probucol spiroquinone | 100 |
| Example 6 | 134 |
| Example 10 | 128 |

As shown in Table 2, it was observed that the THP-1 cells treated with the spiroquinone derivative of Example 6 or 10 (the compound of the present invention) increased about 1.3 times in apoA-1-dependent HDL cholesterol release as compared with the cells treated with probucol spiroquinone.

Test Example 3 mRNA Expression of Intracellular ABCA1

<Test Procedure>

The cells washed with PBS in Test Example 1 were used. From the cells, RNA was extracted with ISOGEN (manufactured by Wako Pure Chemical Industries, Ltd.). By using a Super Script First-Strand Synthesis System for RT-PCR (manufactured by Invitrogen) cDNA was prepared, and the mRNA expression of ABCA1 was assayed by Real Time PCR using ABCA1 specific primer and Power SYBR Green PCR Master Mix (manufactured by Applied Biosystems).

Moreover, the mRNA expression of GAPDH as an internal control was also assayed simultaneously. The mRNA expression level of ABCA1 was standardized as a ratio (%) relative to the mRNA expression level of GAPDH. The mRNA expression level of ABCA1 in the cells treated with the test compound relative to that in untreated cells was calculated and evaluated.

<Results>

The results are shown in Table 3.

TABLE 3

| Test compounds | mRNA Expression level of ABCA1 (relative ratio %) |
|---|---|
| Untreated cell | 100 |
| Probucol spiroquinone | 65 |
| Example 6 | 51 |

As shown in Table 3, the mRNA expression of ABCA1 in the THP-1 cells treated with the spiroquinone derivative of Example 6 was not found, although increased ABCA1 expression (Test Example 1) and HDL production (Test Example 2) were observed in the THP-1 cells. This reveals that the spiroquinone derivative produced in Examples does not increase the ABCA1 expression level itself, but inhibits the ABCA1 decomposition, resulting in elevated intracellular ABCA1 level.

Test Example 4

Toxicity Test

The spiroquinone derivatives were orally administered to mice, respectively, for one week. The existence of abnormality in these mice was studied. As a result, no abnormal findings were observed in all mice.

Thus, it was confirmed in the above-mentioned tests that the compound of the present invention did not increase the ABCA1 expression level itself, but inhibited the ABCA1 decomposition, thereby expressing ABCA1 stably and continuously, and that the compound drastically accelerated the HDL production reaction and was useful for a prophylactic and/or therapeutic agent for hypo-high density lipoproteinemia.

Preparation Example 1

Using the following formulation, a tablet was obtained in accordance with a known manner described in General Rules for Preparations of Japanese Pharmacopoeia XIV.

Formulation Example Per Tablet:

| | |
|---|---|
| Spiroquinone derivative of the present invention | 50 mg |
| Crystalline cellulose | 100 mg |
| Corn starch | 28 mg |
| Magnesium stearate | 2 mg |
| Total amount | 180 mg |

Preparation Example 2

Using the following formulation, a capsule was obtained in accordance with a known manner described in General Rules for Preparations of Japanese Pharmacopoeia XIV.

Formulation Example Per Capsule

| | |
|---|---|
| Spiroquinone derivative of the present invention | 50 mg |
| Lactose | 100 mg |
| Corn starch | 28 mg |
| Magnesium stearate | 2 mg |
| Total amount | 180 mg |

The invention claimed is:
1. A spiroquinone compound represented by the following formula (1):

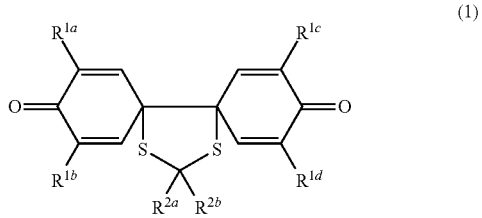

wherein $R^{1a}$, $R^{1b}$, $R^{1c}$ and $R^{1d}$ are the same or different and each represents a hydrogen atom, a halogen atom, an alkyl group which may have a substituent, or an alkoxy group which may have a substituent, and $R^{2a}$ and $R^{2b}$ are the same or different and each represents a hydrogen atom, a carboxyl group, an alkoxycarbonyl group, a carbamoyl group, an N-substituted carbamoyl group, an alkyl group which may have a substituent, an aryl group which may have a substituent, or an aralkyl group which may have a substituent, the groups $R^{2a}$ and $R^{2b}$ may bond together to form a hydrocarbon ring with an adjacent carbon atom, and the hydrocarbon ring may have a substituent, provided that compounds in which all of the groups $R^{1a}$, $R^{1b}$, $R^{1c}$ and $R^{1d}$ are t-butyl groups, and both of the groups $R^{2a}$ and $R^{2b}$ are hydrogen atoms or both of the groups $R^{2a}$ and $R^{2b}$ are methyl groups are excluded; or a pharmacologically acceptable salt thereof.

2. The spiroquinone compound or pharmacologically acceptable salt thereof according to claim 1, wherein the groups $R^{1a}$, $R^{1b}$, and $R^{1d}$ are the same or different and each represents a linear or branched $C_{1-6}$alkyl group which may have a substituent or a linear or branched $C_{1-6}$alkoxy group which may have a substituent.

3. The spiroquinone compound or pharmacologically acceptable salt thereof according to claim 1, wherein the groups $R^{1a}$, $R^{1b}$, and $R^{1d}$ are the same or different and each represents a branched $C_{3-6}$alkyl group which may have a substituent or a branched $C_{3-6}$alkoxy group which may have a substituent.

4. The spiroquinone compound or pharmacologically acceptable salt thereof according to claim 1, wherein the substituent of the alkyl group represented by the groups $R^{2a}$ and $R^{2b}$ is at least one substituent selected from the group consisting of a halogen atom, a hydroxyl group, an alkoxy group, a haloalkoxy group, an acyl group, an acyloxy group, a carboxyl group, an alkoxycarbonyl group, a carbamoyl group, an N-substituted carbamoyl group, a cyano group, and a nitro group.

5. The spiroquinone compound or pharmacologically acceptable salt thereof according to claim 1, wherein the hydrocarbon ring which is formed by the bond of the groups $R^{2a}$ and $R^{2b}$ and the adjacent carbon atom is a 4- to 8-membered saturated or unsaturated hydrocarbon ring, and the hydrocarbon ring has at least one substituent selected from the group consisting of a halogen atom, a hydroxyl group, an alkoxy group, a haloalkoxy group, an acyloxy group, a carboxyl group, an alkoxycarbonyl group, a carboxyalkyl group, an alkoxycarbonylalkyl group, a carbamoyl group, a carbamoylalkyl group, an N-substituted carbamoyl group, an N-substituted carbamoylalkyl group, a cyano group, and a nitro group.

6. The spiroquinone compound or pharmacologically acceptable salt thereof according to claim 1, wherein the groups $R^{2a}$ and $R^{2b}$ are the same or different and each represents a hydrogen atom; a carboxyl group; a $C_{1-6}$alkoxy-carbonyl group; a carbamoyl group; an N-substituted carbamoyl group; a $C_{6-12}$aryl group which may have a $C_{1-4}$alkyl group; a $C_{6-12}$aryl group which may have a $C_{1-4}$alkoxy group; a $C_{6-12}$aryl-$C_{1-4}$alkyl group which may have a $C_{1-4}$alkyl group; a $C_{6-12}$aryl-$C_{1-4}$alkyl group which may have a $C_{1-4}$alkoxy group; a $C_{1-6}$alkyl group; a $C_{1-6}$alkyl group having a halogen atom; a carboxy$C_{1-6}$alkyl group; a $C_{1-6}$alkyl group having a $C_{1-6}$alkoxy-carbonyl group; a carbamoyl$C_{1-6}$alkyl group; or an N-substituted carbamoyl$C_{1-6}$alkyl group; or the groups $R^{2a}$ and $R^{2b}$ bond together to form a 4- to 6-membered saturated or unsaturated hydrocarbon ring with the adjacent carbon atom.

7. The spiroquinone compound or pharmacologically acceptable salt thereof according to claim 1, wherein the groups $R^{1a}$, $R^{1b}$, $R^{1c}$ and $R^{1d}$ are the same or different and each represents a branched $C_{3-6}$alkyl group which may have a substituent or a branched $C_{3-6}$alkoxy group which may have a substituent, and the groups $R^{2a}$ and $R^{2b}$ are the same or different and each represents a hydrogen atom; a carboxyl group; a $C_{1-4}$alkoxy-carbonyl group; a carbamoyl group; an N-substituted carbamoyl group; a $C_{6-10}$aryl group which may have a $C_{1-2}$alkyl group; a $C_{1-4}$alkyl group; a $C_{1-4}$alkyl group having a halogen atom; a carboxy-$C_{1-4}$ alkyl group; a $C_{1-4}$alkoxy-carbonyl-$C_{1-4}$alkyl group; a carbamoyl$C_{1-4}$alkyl group; or an N-substituted carbamoyl$C_{1-4}$alkyl group; or the groups $R^{2a}$ and $R^{2b}$ bond together to form a 4- to 6-membered saturated or unsaturated hydrocarbon ring with the adjacent carbon atom.

8. A process for producing a spiroquinone compound represented by the following formula (1) or a pharmacologically acceptable salt thereof:

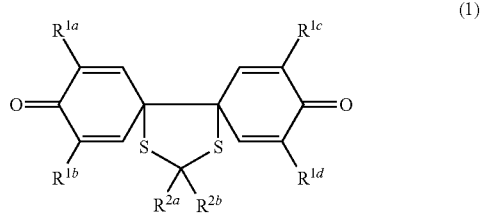

wherein $R^{1a}$, $R^{1b}$, $R^{1c}$ and $R^{1d}$ are the same or different and each represents a hydrogen atom, a halogen atom, an alkyl group which may have a substituent, or an alkoxy group which may have a substituent, and $R^{2a}$ and $R^{2b}$ are the same or different and each represents a hydrogen atom, a carboxyl group, an alkoxycarbonyl group, a carbamoyl group, an N-substituted carbamoyl group, an alkyl group which may have a substituent, an aryl group which may have a substituent, or an aralkyl group which may have a substituent, the groups $R^{2a}$ and $R^{2b}$ may bond together to form a hydrocarbon ring with an adjacent carbon atom, and the hydrocarbon ring may have a substituent, provided that compounds in which all of the groups $R^{1a}$, $R^{1b}$, $R^{1c}$ and $R^{1d}$ are t-butyl groups, and both of the groups $R^{2a}$ and $R^{2b}$ are hydrogen atoms or both of the groups $R^{2a}$ and $R^{2b}$ are methyl groups are excluded;

the process comprising treating a dithioacetal compound represented by the following formula (2) with an oxidant:

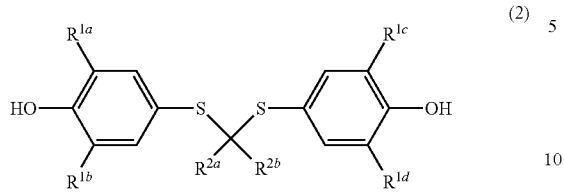

(2)

wherein $R^{1a}$, $R^{1b}$, $R^{1c}$, $R^{1d}$, $R^{2a}$ and $R^{2b}$ have the same meanings as defined above.

9. The process according to claim 8, wherein a mercaptophenol compound represented by the following formula (3a) and/or (3b) is allowed to react with a carbonyl compound represented by the following formula (4) in the presence of an acid to produce the dithioacetal compound represented by the formula (2), and the dithioacetal compound is treated with the oxidant.

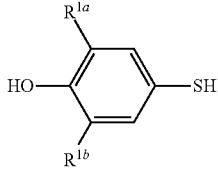

(3a)

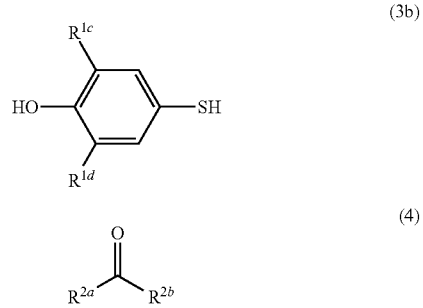

(3b)

(4)

wherein $R^{1a}$, $R^{1b}$, $R^{1c}$, $R^{1d}$, $R^{2a}$ and $R^{2b}$ have the same meanings as defined above.

10. A pharmaceutical composition comprising:
a spiroquinone compound or pharmacologically acceptable salt thereof according to claim 1, and
a carrier.

11. An ABCA1 stabilizer comprising a spiroquinone compound or pharmacologically acceptable salt thereof according to claim 1 as an effective ingredient.

* * * * *

UNITED STATES PATENT AND TRADEMARK OFFICE
CERTIFICATE OF CORRECTION

PATENT NO. : 8,119,686 B2  
APPLICATION NO. : 12/312640  
DATED : February 21, 2012  
INVENTOR(S) : Shinji Yokoyama et al.

Page 1 of 1

It is certified that error appears in the above-identified patent and that said Letters Patent is hereby corrected as shown below:

In claim 2, column 31, line 36, "$R^{1a}$, $R^{1b}$, and $R^{1d}$" should be --$R^{1a}$, $R^{1b}$, $R^{1c}$ and $R^{1d}$--.

In claim 3, column 31, line 42, "$R^{1a}$, $R^{1b}$, and $R^{1d}$" should be --$R^{1a}$, $R^{1b}$, $R^{1c}$ and $R^{1d}$--.

Signed and Sealed this
First Day of May, 2012

David J. Kappos
*Director of the United States Patent and Trademark Office*